(12) United States Patent
Noda

(10) Patent No.: US 11,481,179 B2
(45) Date of Patent: Oct. 25, 2022

(54) INFORMATION PROCESSING APPARATUS AND INFORMATION PROCESSING METHOD

(71) Applicant: SONY CORPORATION, Tokyo (JP)

(72) Inventor: Takuro Noda, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/250,738

(22) PCT Filed: Jun. 26, 2019

(86) PCT No.: PCT/JP2019/025279
§ 371 (c)(1),
(2) Date: Feb. 26, 2021

(87) PCT Pub. No.: WO2020/049838
PCT Pub. Date: Mar. 12, 2020

(65) Prior Publication Data
US 2021/0349675 A1    Nov. 11, 2021

(30) Foreign Application Priority Data
Sep. 7, 2018    (JP) .............................. JP2018-167822

(51) Int. Cl.
*G06F 3/14*     (2006.01)
*A61B 1/00*     (2006.01)
*G06F 3/01*     (2006.01)

(52) U.S. Cl.
CPC ........ *G06F 3/1454* (2013.01); *A61B 1/00039* (2013.01); *A61B 1/00045* (2013.01); *G06F 3/013* (2013.01)

(58) Field of Classification Search
CPC ... G06F 3/1454; G06F 3/013; A61B 1/00039; A61B 1/00045
See application file for complete search history.

(56) References Cited

U.S. PATENT DOCUMENTS

2006/0170652 A1    8/2006    Bannai et al.
2018/0344138 A1    12/2018   Kudo
(Continued)

FOREIGN PATENT DOCUMENTS

| CN | 108778093 A | 11/2018 |
| CN | 109716396 A | 5/2019  |

(Continued)

OTHER PUBLICATIONS

Wang et al., "A Study on Gaze Sharing in Multipoint Multimedia Conferencing Systems", Proceedings of the 77th National Convention of IPSJ. Mar. 17, 2015, pp. 171-172.

(Continued)

*Primary Examiner* — Chong Wu
(74) *Attorney, Agent, or Firm* — Chip Law Group

(57) ABSTRACT

Provided is an information processing apparatus that includes a movement history acquiring section that acquires a movement history, based on an absolute coordinate, of a gazing point of a first user that gazes at a display region, in which the absolute coordinate is in a three-dimensional space displayed in the display region. The information processing apparatus further includes a display controller that controls a display unit that displays the display region to visualize, to a second user, the movement history of the gazing point. This allows the gazing point of the first user to be shared with the second user without hiding a target object.

16 Claims, 15 Drawing Sheets

(56) References Cited

U.S. PATENT DOCUMENTS

| | | | |
|---|---|---|---|
| 2019/0114823 A1 | 4/2019 | Ohba et al. | |
| 2019/0253743 A1* | 8/2019 | Tanaka | G06Q 30/0246 |
| 2019/0354174 A1* | 11/2019 | Young | G06T 15/005 |
| 2019/0354176 A1* | 11/2019 | Horiuchi | A61B 1/05 |

FOREIGN PATENT DOCUMENTS

| | | |
|---|---|---|
| EP | 1686554 A2 | 8/2006 |
| JP | 2006-293605 A | 10/2006 |
| JP | 2009-194697 A | 8/2009 |
| JP | 2015-95802 A | 5/2015 |
| WO | 2017/183353 A1 | 10/2017 |
| WO | 2017/191700 A1 | 11/2017 |
| WO | 2018/051592 A1 | 3/2018 |
| WO | 2018/079166 A1 | 5/2018 |

OTHER PUBLICATIONS

International Search Report and Written Opinion of PCT Application No. PCT/JP2019/025279, dated Aug. 13, 2019, 10 pages of ISRWO.

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2019/025279 filed on Jun. 26, 2019, which claims priority benefit of Japanese Patent Application No. JP 2018-167822 filed in the Japan Patent Office on Sep. 7, 2018. Each of the above-referenced applications is hereby incorporated herein by reference in its entirety.

TECHNICAL FIELD

The present disclosure relates to an information processing apparatus, an information processing method, and a program.

BACKGROUND ART

Recently, a technique has been developed that shares the experience of a first user with a second user through the vision, in a case where there are multiple users.

Patent Literature 1 discloses a technique in which an image expressing a field of view of the first user is generated on the basis of a captured image captured by an imaging unit worn on the head of the first user, and in which the image is presented to the second user. With this method, it is possible to provide an appropriate image to the second user when sharing the experience through the vision between the users.

In addition, in recent years, a technology that displays a motion of a user's eye gaze as a circle, a line, a heat map, or the like may sometimes be used to visualize and analyze the eye gaze.

CITATION LIST

Patent Literature

Patent Literature 1: Japanese Unexamined Patent Application Publication No. 2015-95802

SUMMARY OF THE INVENTION

Problem to be Solved by the Invention

However, in a technique disclosed in Patent Literature 1, although a field of view of a first user is expressed to a second user, it is not possible for the second user to understand the event or the like that the first user focuses on in the field of view, and it is not possible for the second user to sufficiently understand the intention of the first user.

In addition, if a circle or a line, a heat map, or the like is used to represent the focused event in the field of view of the first user, a location viewed by the first user or the second user may be hidden.

For example, in a medical field, an assistant may sometimes operate various devices to perform a surgery while drawing the intention of an operator. At this time, drawing the operator's intention has been left to the assistant's ability, which can influence the smoothness of the surgery, etc. depending on the assistant's skill. In the medical field, an affected site region may be hidden if the event focused by the operator is indicated by the circle, the line, the heat map, or the like, which can possibly influence the surgical operation.

Accordingly, although it is not limited to the medical field, a case in which a target object gazed by the first user is hidden upon expressing the field of view of the first user to the second user can influence the second user sharing the field of view with the first user. Therefore, a technique has been demanded that shares a gazing point of the first user with the second user without hiding the target object.

Means for Solving the Problem

The present disclosure provides an information processing apparatus that includes: a movement history acquiring section that acquires a movement history, based on an absolute coordinate, of a gazing point of a first user that gazes at a display region, in which the absolute coordinate is in a three-dimensional space displayed in the display region; and a display controller that controls a display unit that displays the display region to visualize, to a second user, the movement history of the gazing point.

In addition, the present disclosure provides an information processing method that causes a processor to execute a process that includes: acquiring a movement history, based on an absolute coordinate, of a gazing point of a first user that gazes at a display region, in which the absolute coordinate is in a three-dimensional space displayed in the display region; and controlling a display unit that displays the display region to visualize, to a second user, the movement history of the gazing point.

In addition, the present disclosure provides a program that causes a computer to function as: a movement history acquiring section that acquires a movement history, based on an absolute coordinate, of a gazing point of a first user that gazes at a display region, in which the absolute coordinate is in a three-dimensional space displayed in the display region; and a display controller that controls a display unit that displays the display region to visualize, to a second user, the movement history of the gazing point.

According to the present disclosure, the display unit is controlled to visualize, to the second user, the movement history of the gazing point of the first user.

Effect of the Invention

As described above, according to the present disclosure, it is possible to share the gazing point of the first user with the second user without hiding a target object when the first user gazes at the target object. This allows the second user to understand the intention of the first user with respect to the target object. It is to be noted that the above-described effects are not necessarily limitative, and any of effects described in the present specification or other effects that may be understandable from the present specification may be achieved in addition to the above-described effects or instead of the above-described effects.

MODES FOR CARRYING OUT THE INVENTION

Figure 1:
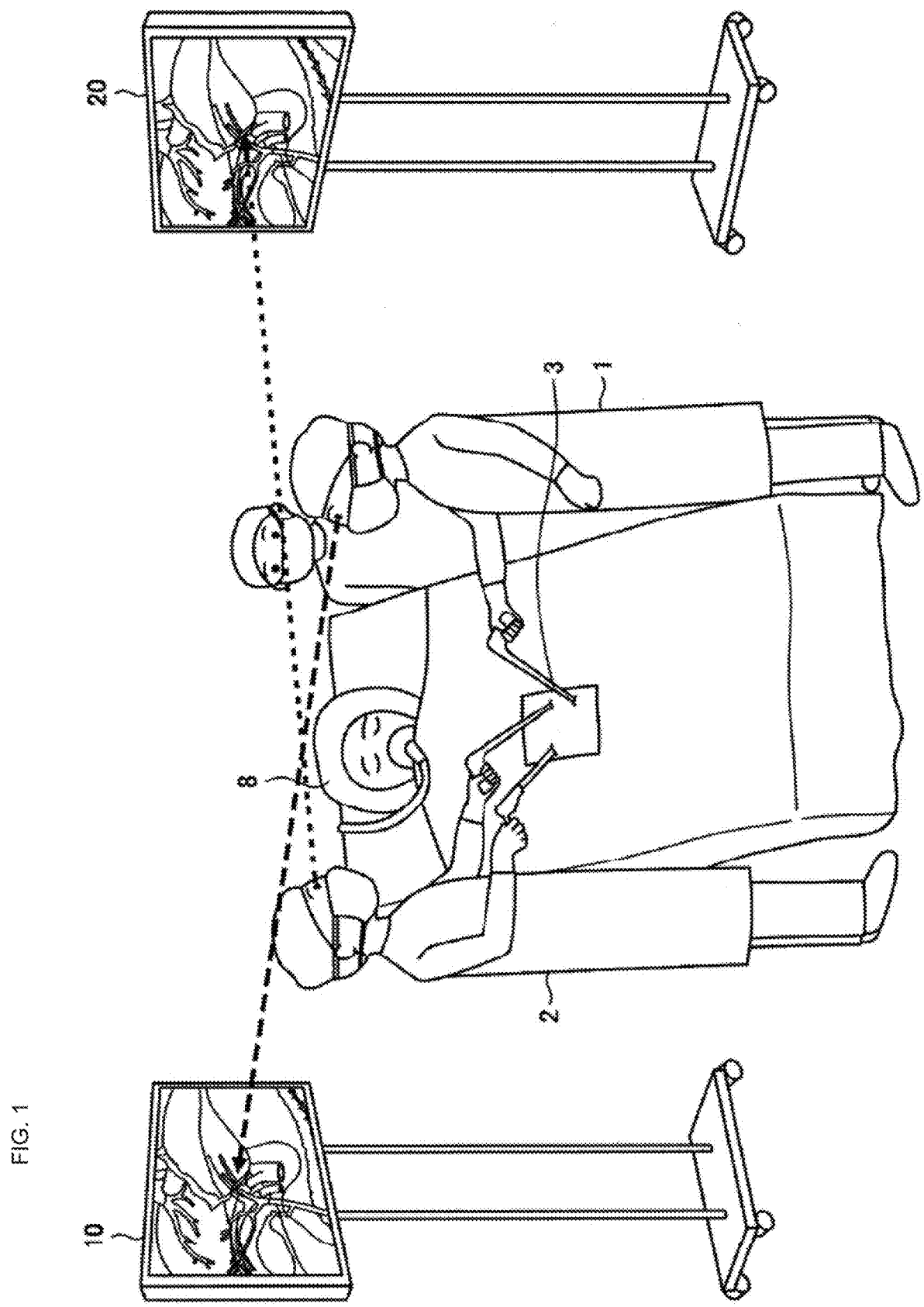
FIG. 1 is a conceptual diagram illustrating an outline of an information processing system according to an embodiment of the present disclosure.

In the following, a preferred embodiment of the present disclosure is described in detail with reference to the accompanying drawings. It is to be noted that in the present specification and the drawings, components having substantially the same functional configuration are assigned the same reference numeral to avoid the repetition of description.

It is to be noted that description is given in the following order.
1. Technical Overview
2. Technical Details
   2.1. Each Configuration and Function
   2.2. Calculation of Movement History
   2.3. Storing of Movement History
   2.4. Displaying of Movement History
3. Operation Flow
4. Modification Examples
   4.1. Operator Wears Loupe-Type Display Unit
   4.2. Operator Wears Loupe-Type Display Unit and Assistant Wears HMD-type Display Unit
   4.3. Operator Wears HMD-Type Display Unit
   4.4. Operator and Assistant Operate Microscope
5. Hardware Configuration Example (1. Technical Overview)

A technique of the present disclosure relates to a technique that visualizes, to a second user, a movement history of a gazing point without hiding a target object when a first user gazes at a target object. In the present embodiment, a medical field will be exemplified, and a scene will be described in which a surgery is performed using an endoscope, where the first user is an operator and the second user is an assistant. However, the technique of the present disclosure is not limited to the medical field.

FIG. 1 is a diagram illustrating a state of a scene of an endoscopic surgery. A patient 8 is placed on a surgical table, and an operator 2 and an assistant 1 stand around the patient 8 to carry out the surgery. The assistant 1 is responsible for controlling an endoscope 3. The assistant 1 controls an affected site region displayed on an assistant monitor 10 while viewing, through the assistant monitor 10 (a display unit 10), a captured image of an affected site (a surgical field) captured by the endoscope 3. Meanwhile, the operator 2 performs the treatment while viewing, through an operator monitor 20, the captured image captured by the endoscope 3.

As described above, in the surgery, the affected site is presented to the operator 2, the assistant 1, and the like as the affected site region through the monitors or the like. In particular, in the endoscopic surgery, the assistant 1 called a scopist appropriately controls the surgical field captured by the endoscope 3, thereby creating an environment in which the operator 2 is able to perform the surgery smoothly. Accordingly, the assistant 1 has been required to understand or infer a location (a gazing point) that the operator 2 is gazing at in the surgical field, and to present the appropriate affected site region to the operator 2.

However, because the understanding or inference of the gazing point depend on the skill of the assistant 1, it has been difficult for the unskilled assistant 1 or the like to present the appropriate affected site region to the operator 2. Therefore, in a technique of the present disclosure, a movement history of the gazing point of a first user exemplified by the operator 2 is visualized and presented, thereby enabling a second user exemplified by the assistant 1 to appropriately understand the intention of the first user. Thus, in the medical field, the movement history of the gazing point of the operator 2 is visualized and presented to the assistant 1 without hiding the affected site, thereby facilitating the assistant 1 to properly understand the intention of the operator 2. The assistant 1 is able to predict a subsequent action to be taken by the operator 2 and provide the operator 2 with an appropriate surgical environment.

(2. Technical Details)
(2.1. Each Configuration and Function)

Figure 2:
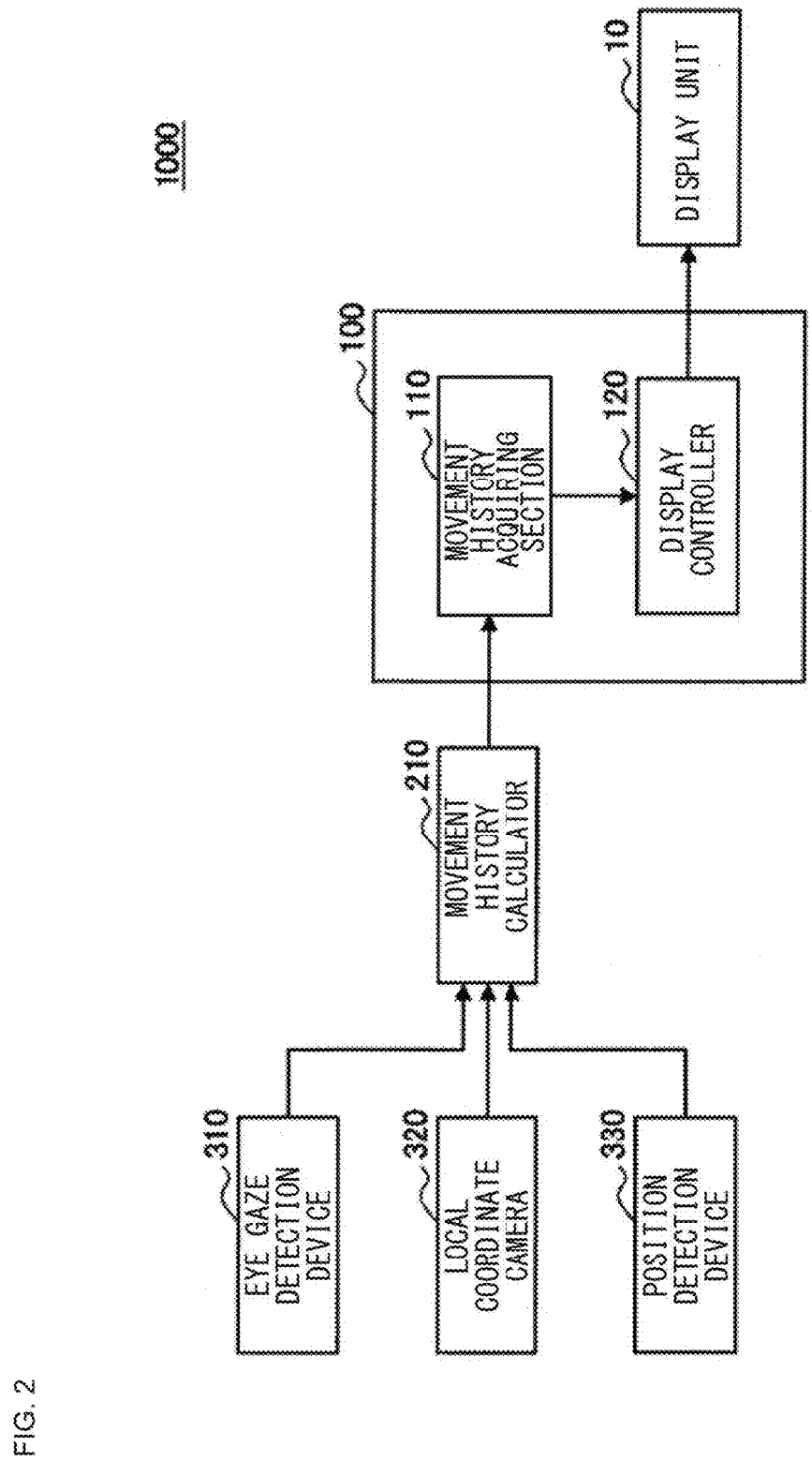
FIG. 2 is a diagram illustrating a configuration of the information processing system according to the embodiment.

Referring to FIG. 2, described next is an information processing system 1000 to which a technique of the present disclosure is applied. FIG. 2 is a block diagram illustrating an example of an apparatus configuration upon performing the surgery described with reference to FIG. 1.

The information processing system 1000 includes an eye gaze detection device 310, a local coordinate camera 320, a position detection device 330, a movement history calculator 210, an information processing apparatus 100, and the display unit 10.

The eye gaze detection device 310 is a device that detects eye gaze information of the operator 2. The eye gaze detection device 310 may be attached to the operator 2 or may be installed in an external environment without being attached to the operator 2. In a case where the eye gaze detection device 310 is to be attached to the operator 2, the eye gaze detection device 310 may be attached to the head or the face of the operator 2 to detect the eye gaze of the operator 2. The eye gaze information contains information on an orientation or a gazing direction of the face of the operator 2. The gaze refers to visual fixation of any location in a display region during viewing of the display region.

The eye gaze information may also be information acquired by detection of eye movement, pupil detection, or the like. For example, the eye gaze information may be acquired by imaging eyes of a user with a camera or the like and performing an image process. A known technique may be used as a technique for detecting the eye gaze information. For example, a pupil corneal reflection method or the like using a corneal reflection image in which light of a light source is reflected in a cornea may be used.

In a case where the eye gaze detection device 310 is installed in the external environment, the eye gaze detection device 310 may be installed in an operating room, for example, on a ceiling or a wall, to detect the eye gaze information of the operator 2. The eye gaze detection device 310 may be an infra-red camera, an imaging unit, etc.

The local coordinate camera 320 has a function of imaging a target object. For example, the local coordinate camera 320 may be provided at a tip of the endoscope 3. The local coordinate camera 320 captures an image of an organ or the like of the patient 8 at the time of the surgery as the target object. The local coordinate camera 320 has a function of capturing an image of the organ and acquiring position information of the organ with respect to the local coordinate camera 320. The position information of the organ may be a spatial coordinate of the organ based on the local coordinate camera 320, that is, a local coordinate. The position information of the organ may also be information on a direction and a distance from the local coordinate camera 320 to the organ. The local coordinate camera 320 may be a stereo-type camera that captures images of the organ from a plurality of angles, and the local coordinate camera 320 acquires the position information of the organ by performing the image process on the captured images captured from the plurality of angles.

In the above description, the local coordinate camera 320 is the imaging unit as an example of the present embodiment. However, the local coordinate camera 320 is not limited in its form as long as it is possible to grasp the position information of the target object. For example, a known sensor or the like that acquires the position information may be used instead of the local coordinate camera 320. Such a sensor may be provided separately from the imaging unit provided in the endoscope 3. The sensor may be a depth sensor, and may acquire the position information from the depth sensor to the organ. The depth sensor may specifically be a sensor, such as a ToF (Time of Flight) sensor, that measures a distance between the target object and the sensor from the time it takes for the projected laser to reciprocate to the target object. In addition, the position information may be acquired by a projection-type device provided with a projector and the imaging unit. In this technique, a pattern projected against the target object by the projector or the like is treated as an image captured by a camera of a projector viewpoint, and triangulation is performed between the image of the projector viewpoint and an image captured by the camera to acquire the position information of the target object. The imaging unit provided in the endoscope 3 is an exemplary surgical imaging unit in the present disclosure.

The position detection device 330 has a function of detecting a position and an attitude of the local coordinate camera 320. A location at which the position detection device 330 is not limited, as long as a position of the position detection device 330 in the three-dimensional space is apparent and as long as it is possible to detect the local coordinate camera 320. For example, the position detection device 330 is installed in the operating room, and performs imaging of the endoscope 3 that has the local coordinate camera 320, and performs an image process of a captured image to detect an absolute coordinate of the local coordinate camera 320 in the three-dimensional space. The position detection device 330 may be an infra-red camera, an imaging unit, etc.

In the above description, the position detection device 330 is the imaging unit as an example of the present embodiment. However, the position detection device 330 is not limited in its form as long as it is possible to grasp the position and the attitude of the local coordinate camera 320. For example, the position detection device 330 may be a magnetic sensor that detects an absolute coordinate of the local coordinate camera 320 by measuring a magnetic field emitted from an excitation coil.

The movement history calculator 210 has a function of calculating a movement history of the gazing point gazed by the operator 2, on the basis of pieces of information acquired by the eye gaze detection device 310, the local coordinate camera 320, and the position detection device 330. A method of calculating the movement history by the movement history calculator 210 will be described later.

The gazing point indicates a point in the display region with respect to the display region, and also indicates a point corresponding to the three-dimensional space with respect to the display region.

The information processing apparatus 100 includes a movement history acquiring section 110 and a display controller 120. The information processing apparatus 100 has a function of acquiring the movement history of the gazing point calculated by the movement history calculator 210 and visualizing the movement history by controlling the display unit 10. The movement history is visualized by the display unit 10, but is so displayed as not to hide the target object displayed in the display region.

The movement history acquiring section 110 acquires the movement history of the gazing point calculated by the movement history calculator 210 and outputs the acquired movement history to the display controller 120. The movement history acquiring section 110 may continuously perform a communication with the movement history calculator 210 at all times to acquire the movement history, or may discontinuously perform the communication to acquire the movement history. The movement history acquiring section 110 may acquire all or a part of the movement history calculated by the movement history calculator 210.

The display controller 120 has a function of acquiring the movement history of the gazing point from the movement history acquiring section 110 and controlling the display unit 10 so as to visualize the movement history. The display controller 120 changes a display style of the movement history to visualize a gazing region. Further, the display controller 120 may vary the display style depending on the display unit 10 to be used. The display styles of the movement history will be described later.

The display unit 10 is controlled by the display controller 120 and has a function of displaying the movement history in the display region. The display unit 10 is not limited in its form as long as the display unit 10 is able to present the captured image captured by the endoscope 3 to the user and visualize the movement history. For example, the display unit 10 may be a display unit used by being attached to the user, such as a head-mounted display (HMD: Head Mounted Display), or may be a display unit, such as a stationary monitor. The HMD is an example of a wearable display unit in the present disclosure.

With the above-described respective configurations, the movement history of a gazing point 113 of the operator 2 may be acquired by the movement history acquiring section 110 of the information processing apparatus 100, and the assistant monitor 10 may be controlled by the display controller 120 to display the movement history to the assistant.

(2.2. Calculation of Movement History)

Figure 3:
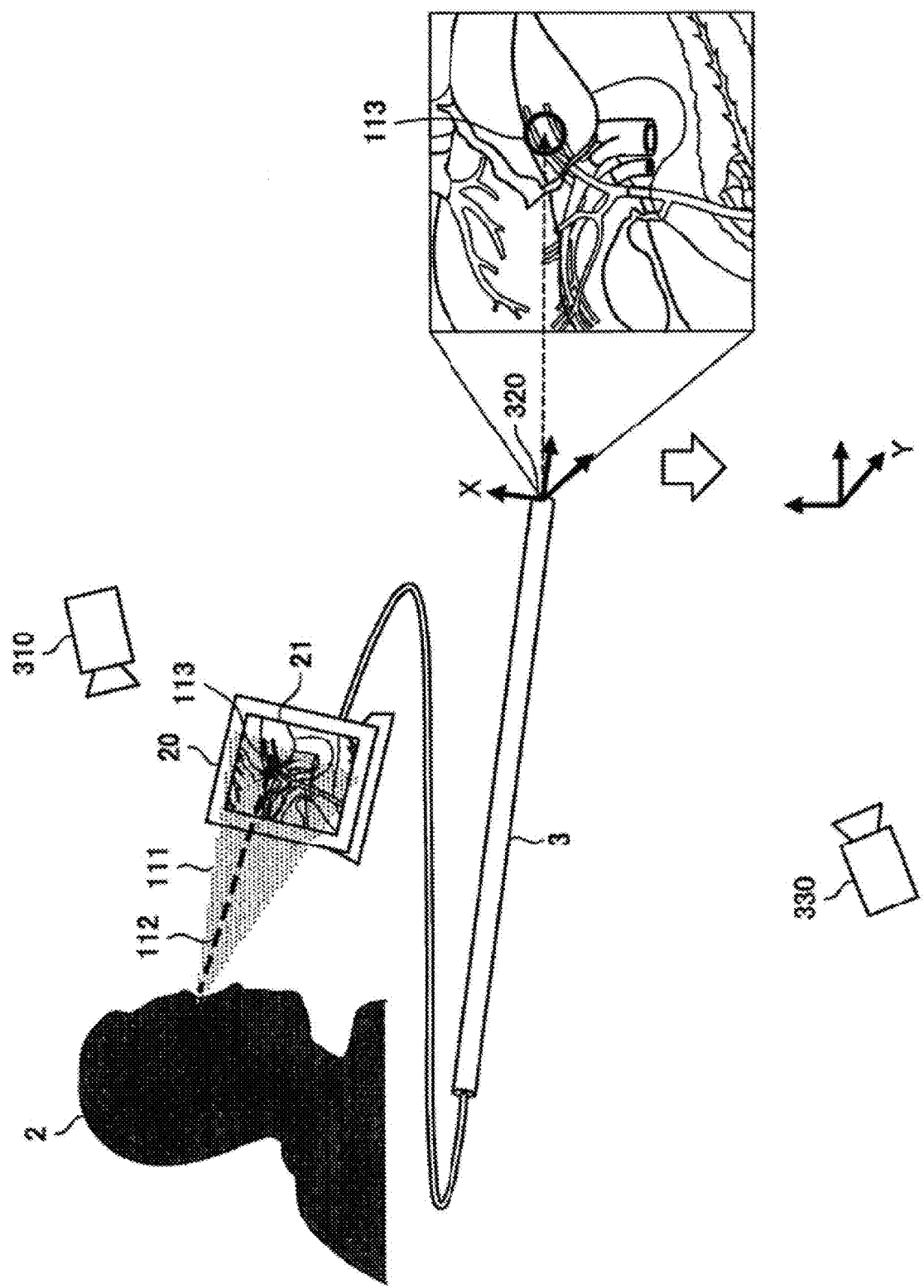
FIG. 3 is a schematic diagram illustrating how a movement history calculator of the information processing system according to the embodiment calculates a movement history.

Referring to FIG. 3, a method in which the movement history calculator 210 calculates the movement history will now be described. FIG. 3 is a schematic diagram depicting how the movement history calculator 210 calculates the movement history. Referring to FIG. 3, the operator 2 performs the surgery on the patient 8 while viewing the operator monitor 20 that displays the captured image acquired by the imaging of the inside of the body of the patient 8 by the endoscope 3. The eye gaze detection device 310 that detects the eye gaze of the operator 2 is installed in the operating room, and the eye gaze detection device 310 detects the eye gaze information of the operator 2. Accordingly, the eye gaze detection device 310 may be installed in the external environment or may be attached to the operator monitor 20.

The tip of the endoscope 3 is provided with the local coordinate camera 320 that performs the imaging of the inside of the body of the patient 8 and detects a position of the organ in the body. The local coordinate camera 320 may be a stereo-type camera. The captured image captured by the local coordinate camera 320 is displayed on the operator monitor 20. The operator 2 gazes at a display region 21 of the operator monitor 20. In FIG. 3, the eye gaze of the operator 2 moves in a viewing range 111 within the display region 21, and a point where the extension of a gazing direction 112 of the operator 2 and the display region 21 intersect with each other is denoted as the gazing point 113.

The local coordinate camera 320 detects the position of the organ of the patient 8 based on the local coordinate camera 320 as the spatial coordinate of a local coordinate system X (hereinafter referred to as a local coordinate). Thus, the local coordinate of the position of the organ corresponding to the display region 21 of the operator monitor 20 is known. Here, the eye gaze detection device 310 acquires the eye gaze information of the operator 2 with respect to the display region 21, and the movement history calculator 210 acquires the gazing direction 112 in which the operator 2 gazes.

The local coordinate camera 320 acquires the position information of the organ from the local coordinate camera 320 as depth information. The depth information includes information on a distance and a direction from the local coordinate camera 320 to the organ. The movement history calculator 210 estimates, from the gazing direction 112 with respect to the display region 21 and the position information of the organ, the local coordinate of the gazing point at which the operator 2 gazes. Note that, in a case where it is not possible to estimate, from the gazing direction and the depth information, the local coordinate which is based on the local coordinate camera 320, the local coordinate of the gazing point may be estimated on the assumption that the organ is distant from the local coordinate camera 320 by a predetermined distance. In addition, the gazing direction with respect to the display region 21 may be estimated from both eye congestion to estimate the local coordinate.

Further, the position detection device 330 that detects the position and the attitude of the local coordinate camera 320 is provided in the operating room. The position detection device 330 acquires, as an absolute coordinate of an absolute coordinate system Y in the three-dimensional space, the position and the attitude of the local coordinate camera 320 in the three-dimensional space. In the local coordinate camera 320, the position of the organ is represented as the local coordinate. Accordingly, knowing the absolute coordinate of the local coordinate camera 320 makes it possible to convert the position of the organ into the absolute coordinate.

The movement history calculator 210 thus estimates that an intersection of a depth of the organ and the gazing direction is the gazing point, on the basis of the depth information of the captured image of the local coordinate camera 320 and the eye gaze information of the operator 2. Specifically, the operator 2 performs the surgery while viewing, in the viewing range 111, the captured image displayed in the display region 21 of the operator monitor 20. The eye gaze detection device 310 detects the gazing direction 112 in which the operator 2 gazes as a surgical site in the viewing range 111. The movement history calculator 210 has already acquired the depth information in which the position of the organ is represented as the spatial coordinate in the captured image to be displayed on the operator monitor 20; hence, it is possible for the movement history calculator 210 to determine the intersection of the gazing direction 112 and the captured image to be displayed on the operator monitor 20 as the gazing point 113. The gazing point 113 is grasped by the movement history calculator 210 as the spatial coordinate of the local coordinate from a point in the display region of the operator monitor 20, and the spatial coordinate of the local coordinate is further converted as the absolute coordinate. By grasping the gazing point 113 in the form of the absolute coordinate, it is possible for the movement history calculator 210 to display the gazing point 113 to the assistant 1 without involving the movement of the gazing point 113 even if the position and the attitude of the local coordinate camera 320 have changed.

(2.3. Storing of Movement History)

Figure 4:
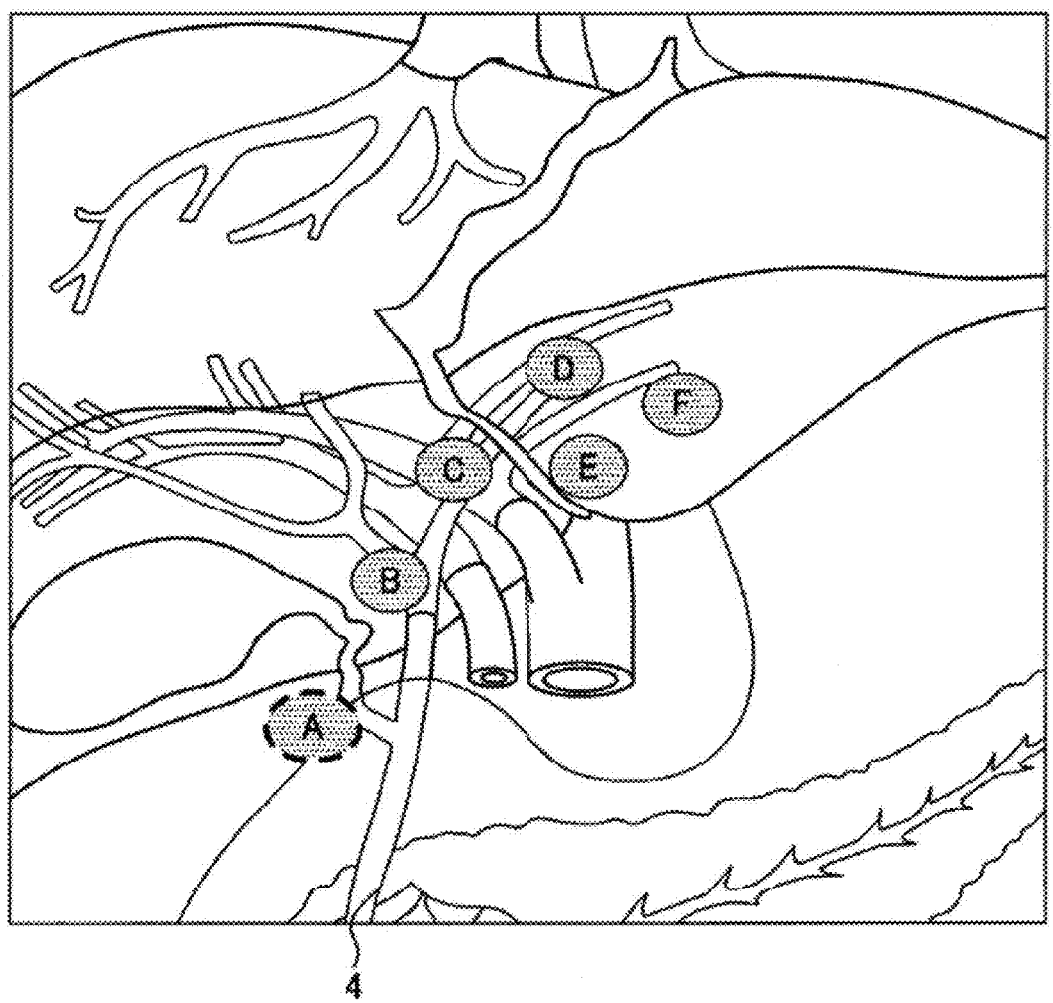
FIG. 4 is a diagram illustrating an exemplary movement history of a gazing point of an operator.
Figure 5:
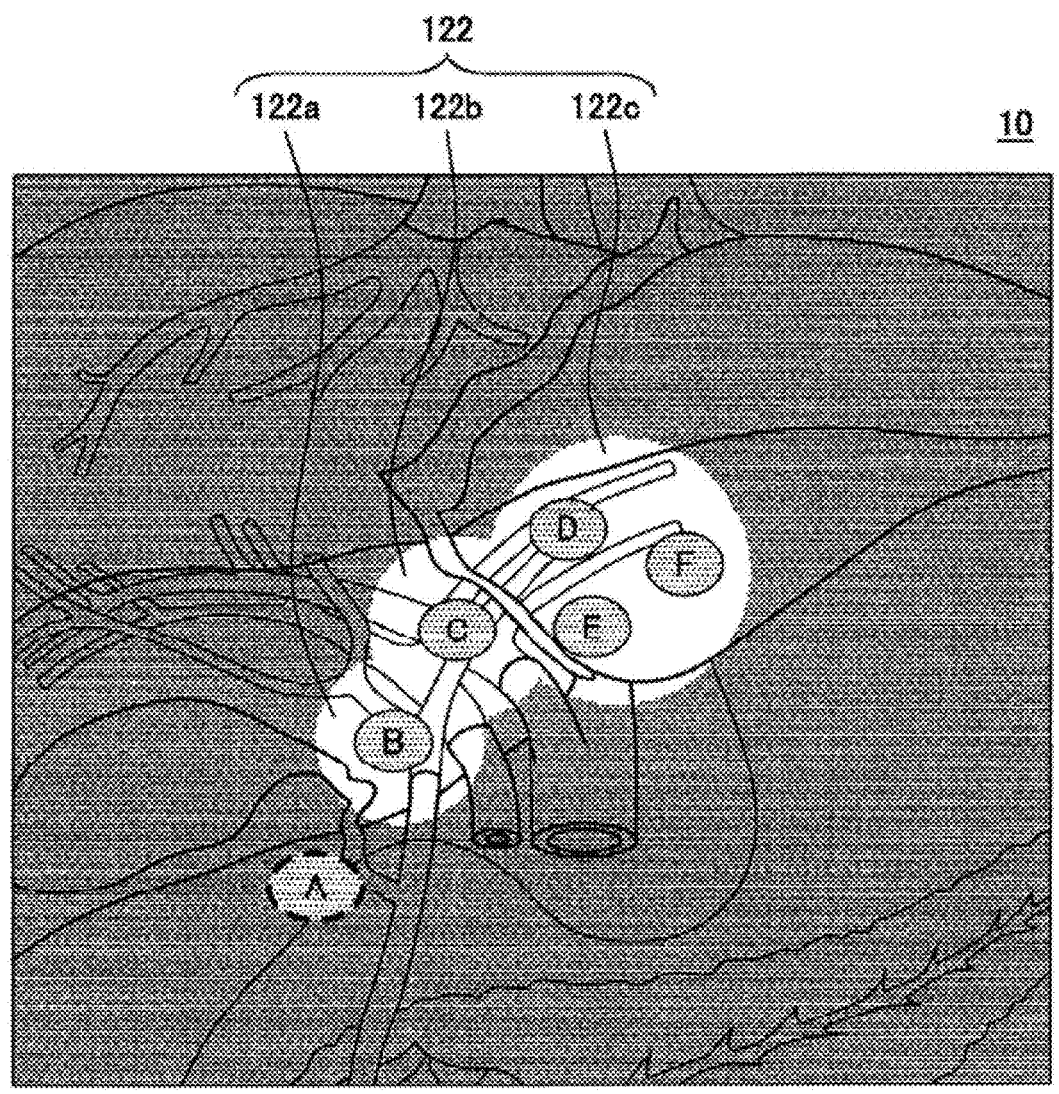
FIG. 5 is a diagram illustrating an exemplary display style of the movement history of the gazing point of the operator.

Referring to FIGS. 4 and 5, a state of the gazing point displayed on the assistant monitor 10 will be described. FIG. 4 is a diagram illustrating the movement history of the gazing point, and FIG. 5 is a diagram illustrating an exemplary display style in which the movement history of the gazing point is visualized. Referring to FIG. 4, the gazing point of the operator 2 moves along an organ 4 in the order of a gazing point A, a gazing point B, a gazing point C, a gazing point D, a gazing point E, and a gazing point F. These gazing points are configured by the predetermined number of gazing points. For example, the predetermined number of gazing points may be used for displaying, retroactively from the most recent gazing point. In an example given in FIGS. 4 and 5, the oldest gazing point A of the gazing points is not used for the displaying, but from the gazing point B to the gazing point F are used for the displaying. Further, when a gazing point is newly acquired, the gazing point B which is the next oldest gazing point is not used for the displaying. In this way, the gazing points used for the displaying are updated.

FIG. 5 illustrates the captured image and the movement history of the gazing point displayed on the assistant monitor 10. The assistant 1 is able to understand the intention of the operator 2 through understanding the movement history of the gazing point displayed on the assistant monitor 10.

In the assistant monitor 10 illustrated in FIG. 5, a predetermined region including the gazing point B in the display region is displayed as the gazing region, and is distinguished from a region other than the gazing region. The predetermined region may be a region including the gazing point and having any distance from the gazing point. The predetermined region may have a circular form centered on the gazing point. For example, in FIG. 5, a gazing region 122a including the gazing point B, a gazing region 122b including the gazing point C, and a gazing region 122c including the gazing point D, the gazing point E, and the gazing point F are displayed in the display region. A region other than the gazing region 122 in the display region is displayed at a brightness lower than that of the gazing region 122. In this manner, the gazing region 122 is displayed in the display style different from that of the region other than the gazing region. The gazing region and the region other than the gazing region are displayed in different display styles, allowing the assistant 1 to recognize the gazing region and the region other than the gazing region and to move the endoscope 3 at the appropriate position and attitude. At this time, a process such as non-displaying of the region other than the gazing region is not performed, and the region other than the gazing region is displayed on the assistant monitor 10 as well. Accordingly, in the medical field such as the surgery, the affected site region is presented to the assistant 1 without being hidden, making it possible to quickly notice abnormalities or the like of the region other than the gazing region.

The gazing region of the gazing point D, the gazing region of the gazing point E, and the gazing region of the gazing point F are overlapped with the gazing region 122c. The gazing region may be so displayed that the display regions corresponding to the respective gazing points are overlapped with each other. Further, for the gazing region, a point having equal distances from a plurality of gazing points may be treated as one gazing point, and the gazing region may include such one gazing point. For example, a region of 2 degrees from the user's gazing point may be treated as a high-resolution region, and the region corresponding to the high-resolution region may be treated as the gazing region.

In FIG. 5, the gazing region including the gazing point A is not displayed as the movement history because the gazing point A is the oldest gazing point, and the gazing point B to the gazing point F which are the latest gazing points are displayed as the movement history.

Thus, instead of displaying only the most recent gazing point, the past gazing points are displayed to display the movement history, allowing the assistant 1 to estimate the intention of the gazing of the operator 2. However, if a large amount of past gazing points are displayed, it becomes difficult to understand where the most recent gazing point is. Accordingly, the movement history of the gazing points exceeding the predetermined number is not displayed.

(2.4. Displaying of Movement History)

The movement history of the gazing point may be displayed in various display styles on the display unit 10 by the display controller 120. The display controller 120 controls the display unit 10 such that the gazing region including the gazing point in the display region and the region other than the gazing region are displayed in different display styles. By the display style, it is possible to increase visibility of the gazing region as compared with the visibility of the region other than the gazing region. The visibility indicates a level of easiness of viewing when the assistant 1 visually recognizes the captured image displayed in the display region. It is possible to attract the attention of the assistant 1 to the gazing region by increasing the visibility of the gazing region. For example, it is possible to make the visibility different between the gazing region and the region other than gazing region in each pixel in the display region, by the saturation, the brightness, the resolution, and the like.

The higher the saturation, the clearer the color display becomes, and the lower the saturation, more monochromatic the displaying becomes. Therefore, the visibility of the gazing region may be increased by making the saturation of the gazing region higher than the saturation of the region other than the gazing region.

The higher the brightness, whiter the displaying becomes, and the lower the brightness, blacker the displaying becomes. Therefore, the visibility of the gazing region may be increased by increasing the brightness of the gazing region.

The higher the resolution is, the higher the definition is, and the lower the resolution is, the lower the definition is. Therefore, the visibility of the gazing region may be increased by making the resolution of the gazing region higher than the resolution of the region other than the gazing region.

Figure 6:
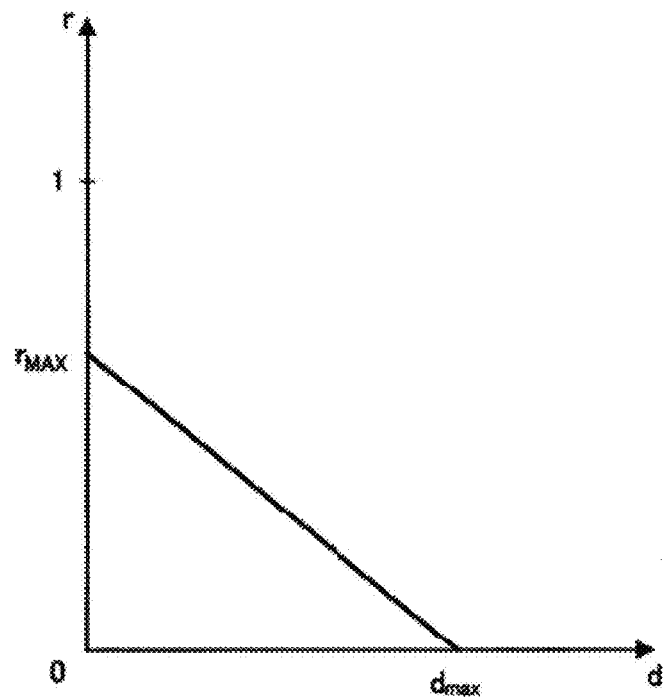
FIG. 6 is a diagram illustrating an example of a parameter related to the display style of the movement history of the gazing point.

For example, with reference to FIG. 6, the level of display style of the gazing region and that of the region other than the gazing region will be described. As illustrated in FIG. 6, for example, the displaying of the gazing region by the color display and the monochrome display may involve a change in color level in accordance with a distance d from the gazing point to each of the pixels. The display style illustrated in FIG. 6 exemplifies an increase in visibility by the saturation described above.

FIG. 6 illustrates a relationship between the distance d from the gazing point and a color level r, and illustrates a tendency that the color level r decreases as the distance d increases. In other words, the color level r may be so displayed and controlled as to have a maximum color level $r_{MAX}$ when the distance to the gazing point is zero and becomes zero at a maximum radius $d_{max}$. By this method, the color level r obtained from each gazing point may be calculated and added for each of the pixels to make the display style of the gazing region and that of the region other than the gazing region different.

Thus, the color level r increases, the color property increases, and the visibility increases for any pixel in which the distances from the respective gazing points more overlap with each other, Note that, here, an upper limit is set for the maximum color level $r_{MAX}$, and the maximum color level $r_{MAX}$ may be displayed in a case where a value exceeding the upper limit is calculated as a value of the color level r.

In addition, in general, in a case where the color hue of each of the pixels includes red R, green G, and blue B, the monochrome hue that performs monochromatizating thereof is calculated by ((0.299×R)+(0.587×G)+(0.114×B)). At this time, the hue to be drawn on each of the pixels as the display style of the gazing region may be expressed by the following expression (1).

((color hue)×(color level r))+((monochrome hue)× (1−(color level r)))     (1)

In the expression (1), the term ((monochrome hue)×(1−color level r)) may be further multiplied by a coefficient greater than zero and less than one to relatively increase the color level. Specifically, by multiplying the coefficient by 0.5, the monochrome level may be halved, and an influence of the monochrome hue of the region other than the gazing region in the display region may be weakened to increase the visibility of the pixel of the gazing region that displays the color hue.

Figure 7:
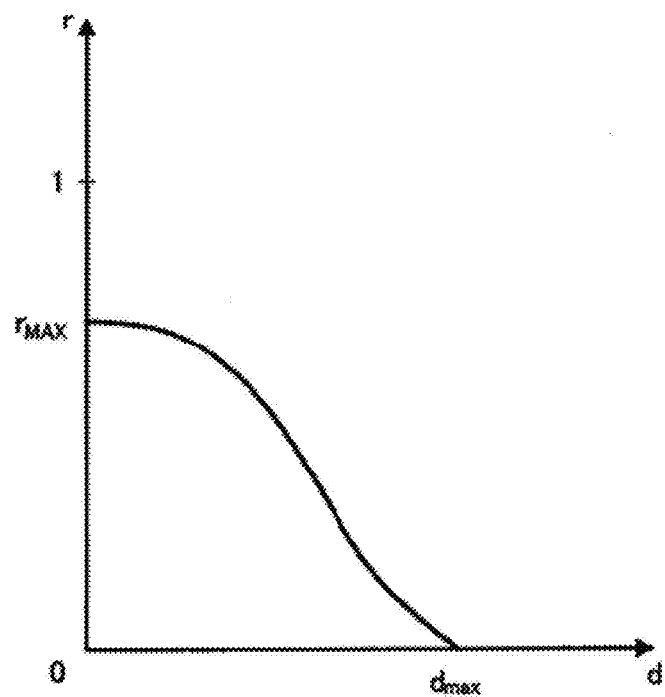
FIG. 7 is a diagram illustrating an example of a parameter related to the display style of the movement history of the gazing point.

Although FIG. 6 illustrates the display style in which the color level r linearly decreases in accordance with the distance d, a relationship between the distance d and the color level r may be a relationship drawn by a smooth curved line as illustrated in FIG. 7. In FIG. 7, the color level is higher in the condition where the distance d from the gazing point is closer as compared with FIG. 6. By this method, it is possible to more preferentially display in color the region in which the distance d is closer to the gazing point as compared with FIG. 6, and the visibility of a portion closer to the gazing point increases.

The above-described gazing region is represented in a circular shape with the gazing point being the center, but the gazing region may be represented in another figure. In addition, a size of the figure may be determined on an as-necessary basis. As the figure becomes larger, it is possible to attract the attention of the assistant 1 to a wider range of the affected site region, and the assistant 1 becomes more aware of a change in the affected site, etc. As the figure becomes smaller, the attention of the assistant 1 is more attracted to the center of the gazing point, allowing the assistant 1 to address a fine change in position of the endoscope 3.

Figure 8:
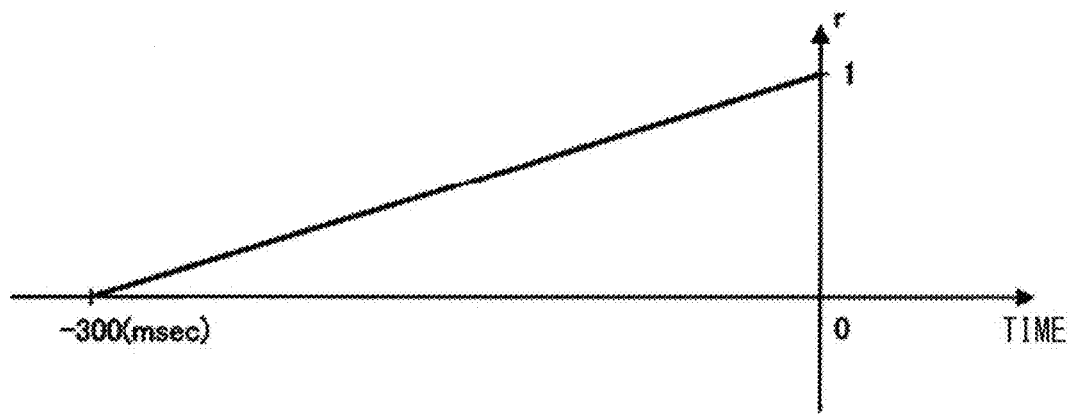
FIG. 8 is a diagram illustrating an example of a parameter related to the display style of the movement history of the gazing point.

The display style of the gazing region is not limited to the distance d from the gazing point as described above, and may be determined by the elapsed time from the occurrence of the gazing point. For example, as illustrated in FIG. 8, the color level r may be changed over time. According to FIG. 8, the color level r of the gazing point 300 msec prior to the current is zero, and the color level r becomes one proportionally as the time approaches the current time. Note that the color level may be maximum when the color level r becomes one. That is, the gazing point 300 msec earlier is displayed as the monochrome display for the region other than the gazing region, and the gazing point 300 msec later is displayed in color and displayed as the gazing region. As the occurrence of the gazing point approaches the current, the visibility increases because the gazing region is displayed in color, and it is possible to understand the order of the movement history of each of the gazing points as well. FIG. 8 illustrates an example in which the color display or the monochrome display is switched on the basis of 300 msec as an example. This is because, in eye gaze detection, if the eye gaze is concentrated at the same location for about 150 msec to 200 msec, it is determined that the point is gazed (fixated). By setting the elapsed time of 300 msec, which has elapsed from the gaze determination reference, as the criteria of the elapsed time of the displaying of the gazing region, it is possible to display an accurate gaze determination. The criteria for displaying the gazing region may be appropriately set in accordance with an environment to which a technique of the present disclosure is applied, or may be appropriately set in accordance with the user, etc.

Figure 9:
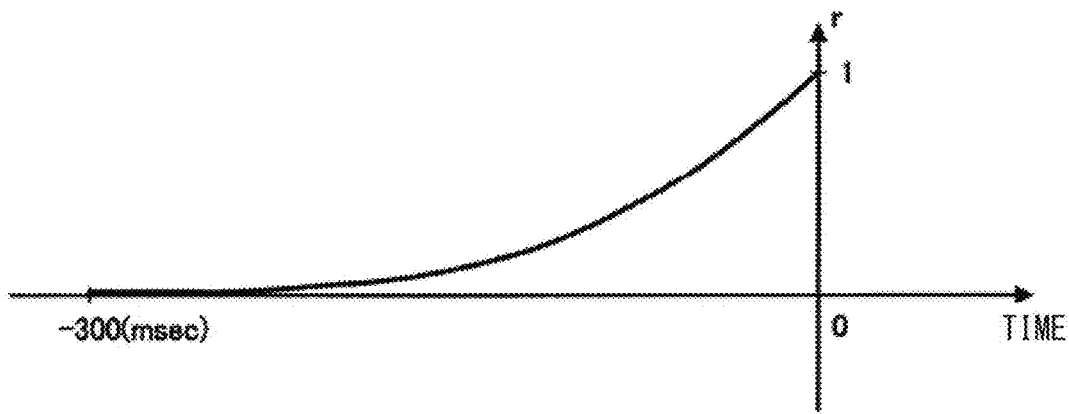
FIG. 9 is a diagram illustrating an example of a parameter related to the display style of the movement history of the gazing point.
Figure 10:
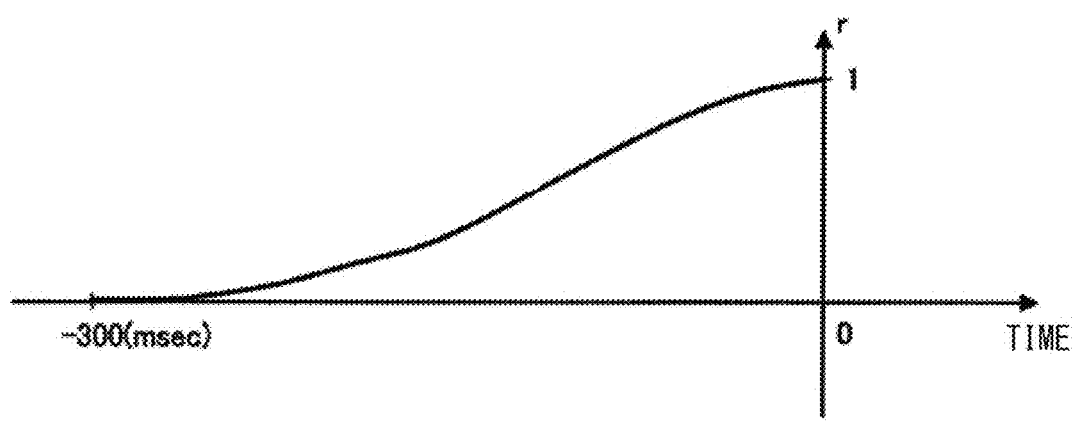
FIG. 10 is a diagram illustrating an example of a parameter related to the display style of the movement history of the gazing point.

Further, as illustrated in FIGS. 9 and 10, the color level r may be zero in the gazing point 300 msec prior to the current, and as the time approaches the present time, the color level r may become one by drawing a gentle curve. The display style of the movement history illustrated in FIG. 9 increases the visibility of the gazing point closer to the current as compared with the display style illustrated in FIG. 10. Meanwhile, in the display style of the movement history illustrated in FIG. 10, the visibility is increased over a wider period of time as compared with the display style illustrated in FIG. 9.

Figure 11:
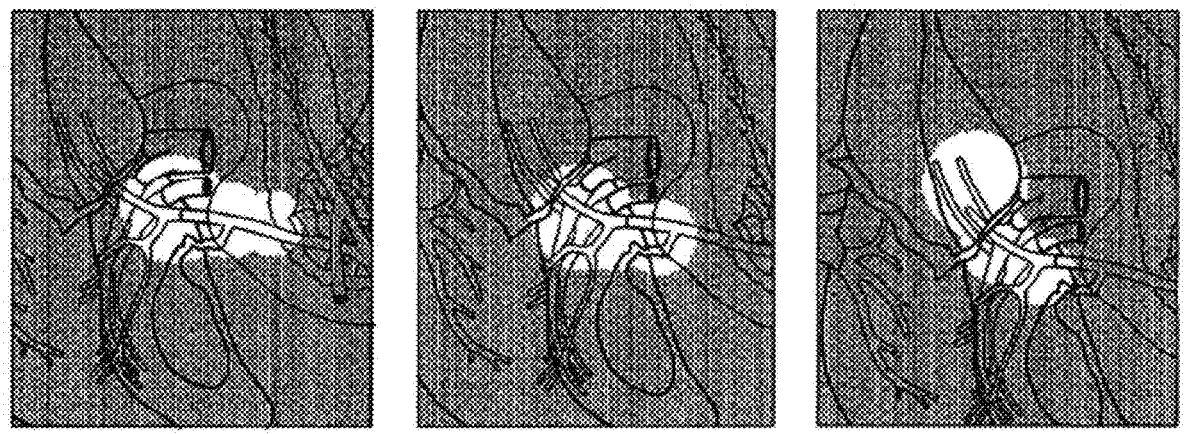
FIG. 11 is a diagram illustrating a state in which the movement history of the gazing point corresponding to an elapse of time is displayed in a display region of an assistant monitor.
Figure 11:
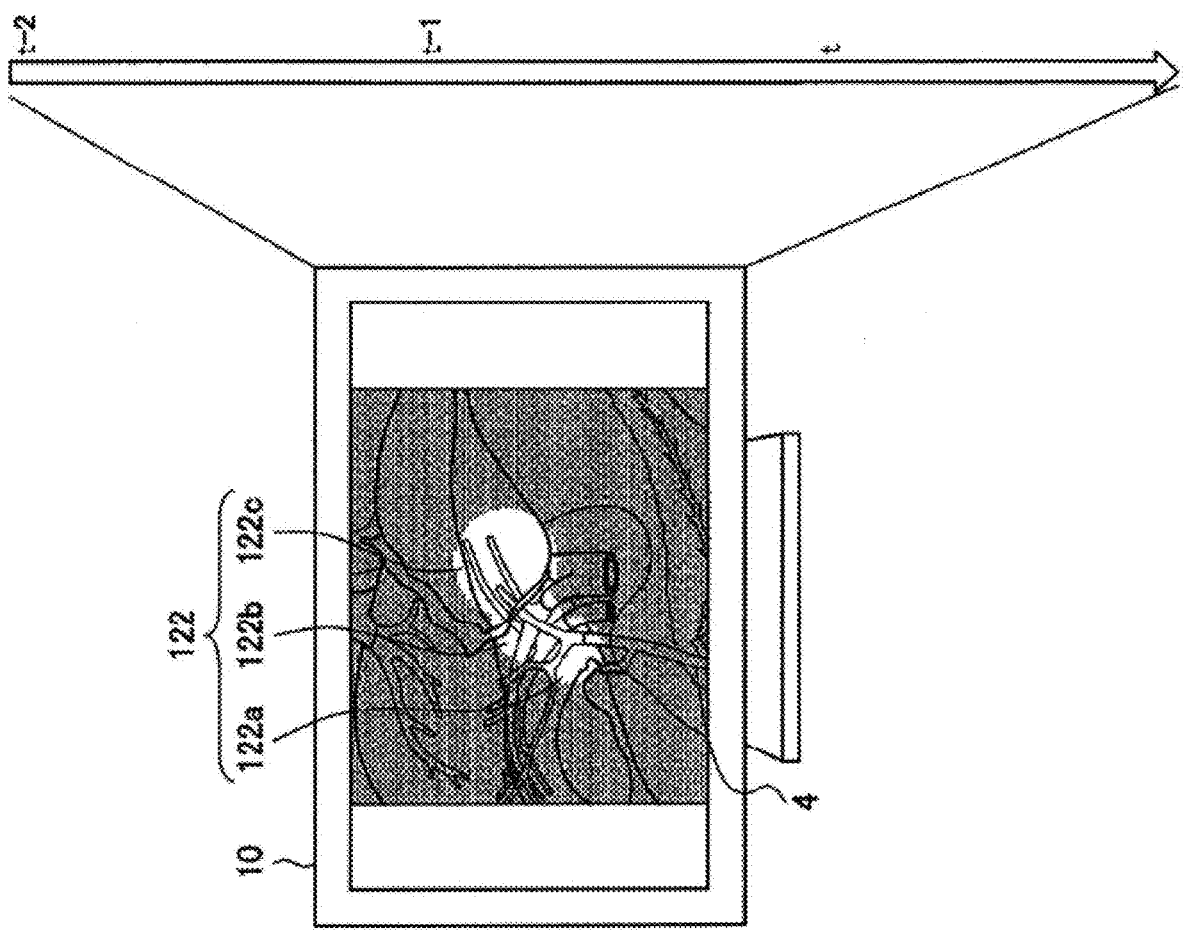

Next, referring to FIG. 11, the displaying of the movement history corresponding to control of the endoscope 3 by the assistant 1 will be described with reference to the elapse of time. FIG. 11 is a diagram illustrating a state in which the movement history of the gazing point corresponding to the elapse of time is displayed in the display region of the assistant monitor 10.

FIG. 11 illustrates the display style of the movement history at each time point, with a time point tracing back to the past in the order from a current time point t being a past time point t-1 and a past time point that is prior to the past time point t-1 being a past time point t-2. The display region of the assistant monitor 10 displays the affected site region of the patient 8 and visualizes the movement history of the gazing point of the operator 2. The gazing point of the operator 2 rises along the organ 4 from a lower side to an upper side of the display region. In the display region, a gazing region 122a, a gazing region 122b, and a gazing region 122c are displayed as the movement history while partially overlapping each other.

Referring to FIG. 11, a position of the target object displayed in the captured image is changed from the past time point t-2 through the past time point t-1 to the current time point t. This is because the position and the attitude of the endoscope 3 has changed and an angle of view of the endoscope 3 has changed accordingly. The position and the attitude of the endoscope 3 so changes from the past time point t-2 through the past time point t-1 to the current time point t as to image an upper part from a lower part of the organ 4. Meanwhile, the movement history of the gazing point is displayed from the past time point t-2 through the past time point t-1 to the current time point t, without linking with the movement of the endoscope 3 from the lower part to the upper part of the organ 4. This is because the movement history of the gazing point is represented in the form of the absolute coordinate. If the movement history of the gazing point remains the local coordinate, the changes in the position and the attitude of the endoscope 3 result in the movement of the gazing point as well. Therefore, by converting the gazing point from the local coordinate into the absolute coordinate, it is possible to display the gazing point without linking the gazing point to the motion of the position and the attitude of the endoscope 3.

(3. Operation Flow)

Figure 12:
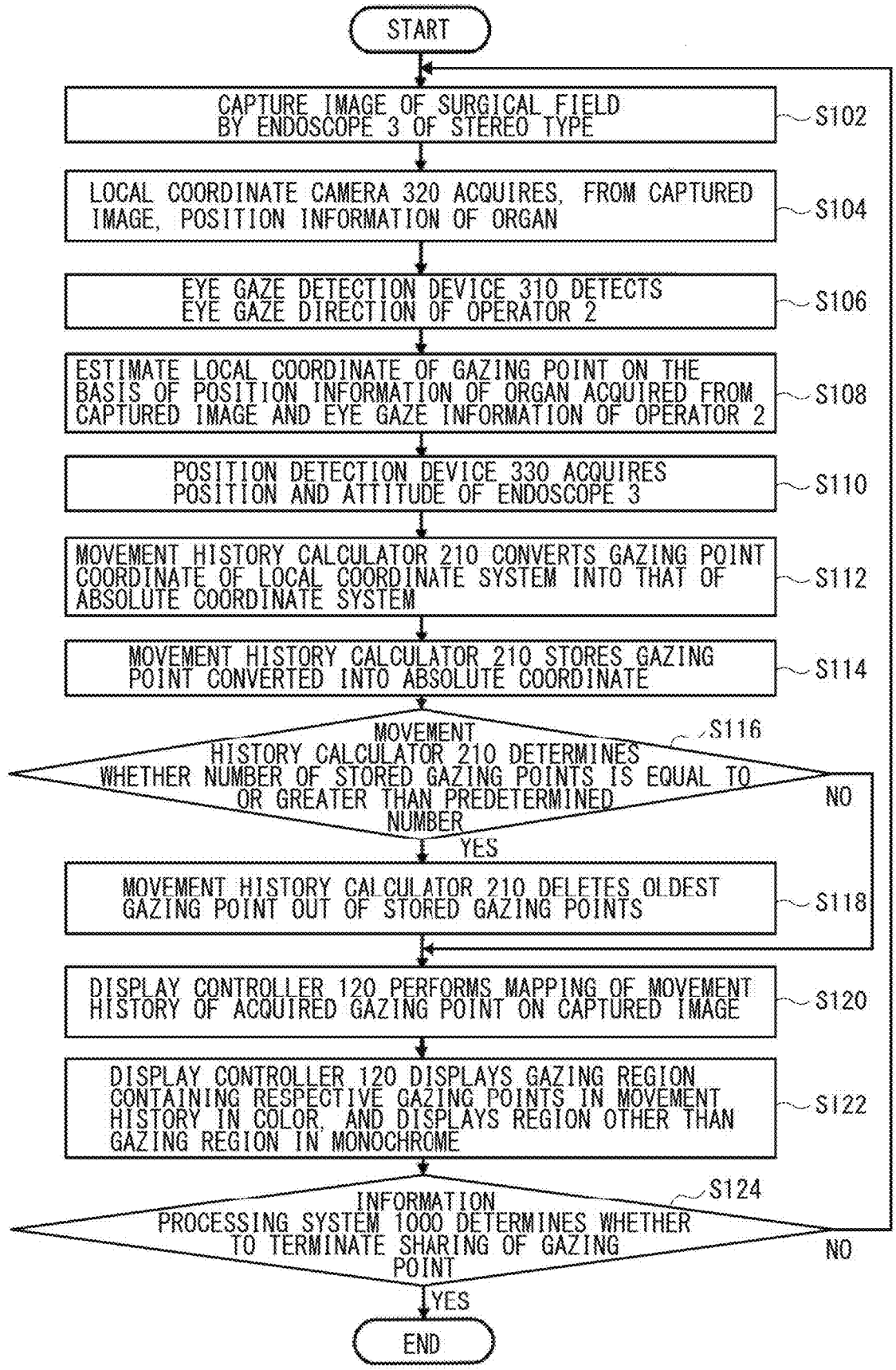
FIG. 12 is a diagram illustrating an operation flow of the information processing system according to the embodiment.

The respective configurations of the information processing system 1000 have been described above. Next, an operation flow of the information processing system 1000 will be described with reference to FIG. 12. FIG. 12 is a flowchart illustrating a process of display control in the present embodiment.

First, an image of the surgical field of the patient 8 is captured by the endoscope 3 provided with the local coordinate camera 320 (S102). The local coordinate camera 320 may be a plurality of imaging units provided in the endoscope 3, and may be of a stereo type. Note that, in the following, an operation flow in a case of performing gazing point sharing is described, and the captured image captured by the imaging unit is displayed on the display unit as it is in a case of where the gazing point sharing is not performed. The instructions for sharing and cancelling the sharing of the gazing point with respect to the information processing system 1000 may be performed by the operator 2 or may be performed by the assistant 1. A change in the display style at this time may involve a gradually change in the display style in accordance with the instructions of sharing and cancelling the sharing of the gazing point.

When the sharing of the gazing point is instructed, the local coordinate camera 320 acquires, from the captured image, the position information such as the position of the organ in the surgical field of the patient 8 (S104). In this case, the position information such as the position of the organ may be represented as the spatial coordinate that is based on the position of the local coordinate camera 320. The position of the organ includes information such as a depth of each point at any point.

Next, the eye gaze detection device 310 detects the eye gaze information of the operator 2 (S106).

Next, the movement history calculator 210 estimates the local coordinate of the gazing point, on the basis of the position information of the organ acquired from the captured image and the eye gaze information of the operator 2 with respect to the display region of the operator monitor 20 (S108).

Next, the position detection device 330 detects the position and the attitude of the endoscope 3. By detecting the position and the attitude of the endoscope 3, the position and the attitude of the endoscope 3 is acquired in the form of the absolute coordinate (S110).

Next, because the position and the attitude of the endoscope 3 are acquired in the form of the absolute coordinate, the movement history calculator 210 converts the local coordinate of the gazing point into the absolute coordinate (S112).

Next, the movement history calculator 210 stores the gazing point converted into the absolute coordinate (S114).

Next, the movement history calculator 210 determines whether the number of stored gazing points has exceeded the predetermined number (S116). If the number of stored gazing points exceeds the predetermined number (S116/Yes), the movement history calculator 210 causes the process to proceed to the next process.

Next, the movement history calculator 210 deletes the oldest gazing point out of the stored gazing points (S118). Note that, if the number of stored gazing points is less than the predetermined number (S116/No), the movement history calculator 210 causes the process to proceed to the next process without performing the step (S118) of deleting the gazing point.

Next, the movement history acquiring section 110 of the information processing apparatus 100 acquires the movement history of the gazing point, and the display controller 120 performs mapping of the movement history on the captured image displayed in the display region of the display unit 10.

Next, the display controller 120 displays the gazing region containing the respective gazing points in the movement history in color, and displays the region other than the gazing region in monochrome (S122).

Next, the information processing system 1000 determines whether to terminate the sharing of the gazing point (S124). If the information processing system 1000 determines to terminate the sharing of the gazing point (S124/Yes), the operation of sharing the gazing point is terminated. Further, if the information processing system 1000 determines not to terminate the sharing of the gazing point (S124/No), the captured image is acquired from the endoscope 3 again (S102) to repeat the operation up to the above continuously. The determination of whether or not to terminate the sharing of the gazing point may be made on the basis of whether or not the information processing system 1000 has acquired the instructions to cancel the sharing of the gazing point from the assistant 1 or the operator 2, for example.

The configuration and the operation flow of the information processing system 1000 according to this embodiment have been described. Although the present embodiment exemplifies that the movement history of the gazing point of the operator is displayed in real time, the movement history of the gazing point may be displayed by being recorded together with the captured image captured by the imaging unit and reproduced by the display unit or the like. At this time, the captured image gazed by the operator, the position and the attitude of the endoscope, and the absolute coordinate of the gazing point are recorded in the information processing system 1000.

(4. Modification Examples)

In this section, examples of specific examples of the display unit 10 during the surgery will be described separately for each scene. The display unit 10 is not limited only to a case where the display unit 10 described in the above embodiment is the monitor display unit, but may be any of various wearable terminals to be attached to and used by the user.

(4.1. Operator Wears Loupe-Type Display Unit)

Figure 13:
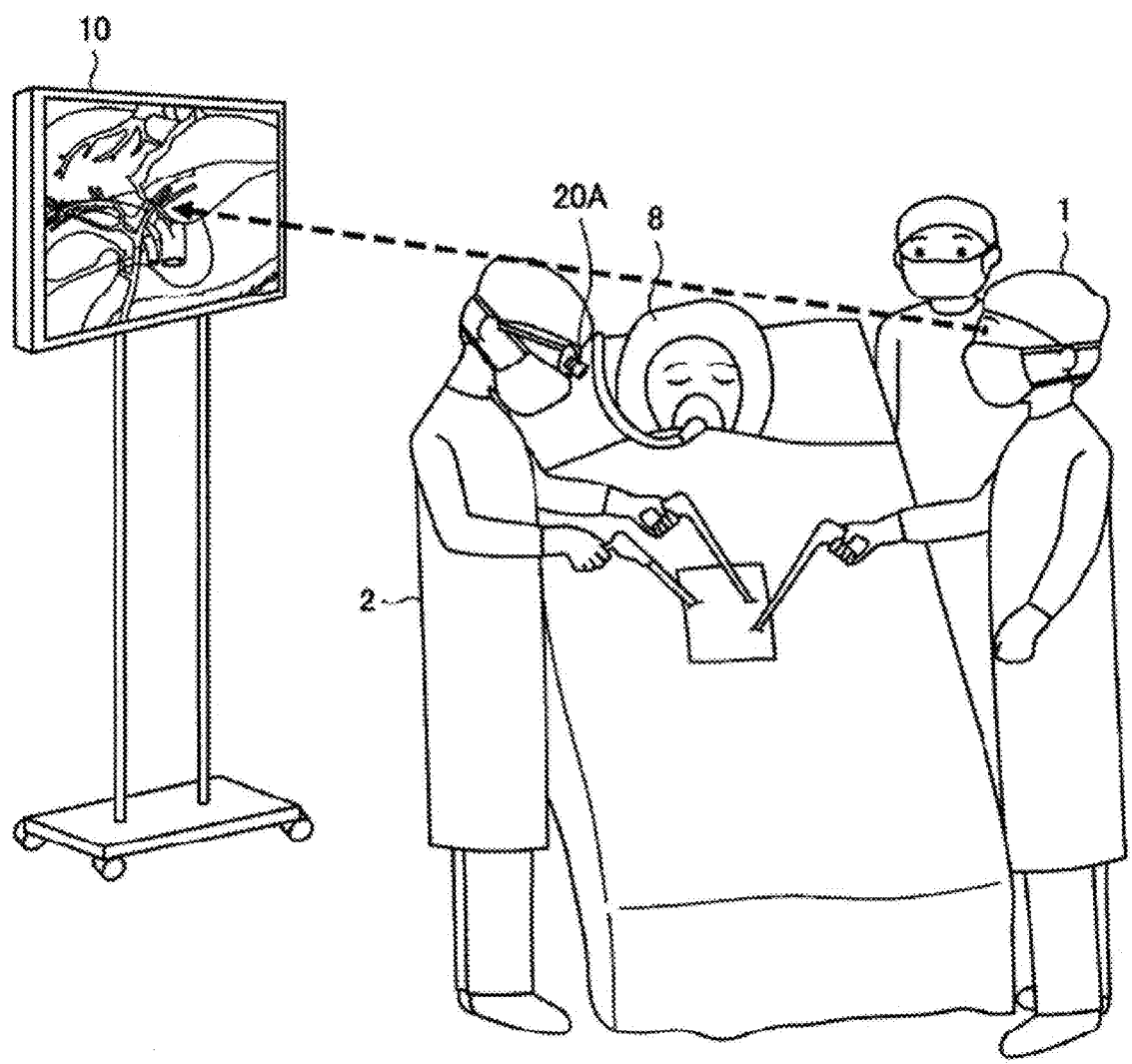
FIG. 13 is a diagram illustrating an exemplary modification example of the information processing system according to the embodiment.

Referring to FIG. 13, the information processing system 1000 in a case where the operator 2 wears a loupe-type first display unit 20A will be described. FIG. 13 is a diagram illustrating an outline of the information processing system 1000 in a case where the operator 2 wears the loupe-type first display unit 20A.

In FIG. 13, the assistant 1 and the operator 2 surround the patient 8 to perform the surgery. The surgery may be, for example, a brain surgery. The operator 2 as the first user wears the loupe-type first display unit 20A. The assistant 1 as the second user performs the surgery while viewing the assistant monitor 10. The loupe-type first display unit 20A is provided with a loupe built-in camera (not illustrated) as the local coordinate camera. The captured image captured by the loupe built-in camera may be displayed on the loupe-type first display unit 20A and the assistant monitor 10. The loupe-type first display unit 20A may have a transmission type display region.

The loupe-type first display unit 20A is further provided with a loupe built-in eye gaze detector (not illustrated) as the eye gaze detection device 310. The position detection device 330 that performs imaging of the loupe-type first display unit 20A may be installed in an operating room or the like.

On the basis of pieces of information acquired from the eye gaze detection device 310, the local coordinate camera 320, and the position detection device 330, the assistant monitor 10 displays the captured image, thereby visualizing and displaying the movement history of the gazing point of the operator 2.

(4.2. Operator Wears Loupe-Type Display Unit and Assistant Wears HMD-Type Display Unit)

Figure 14:
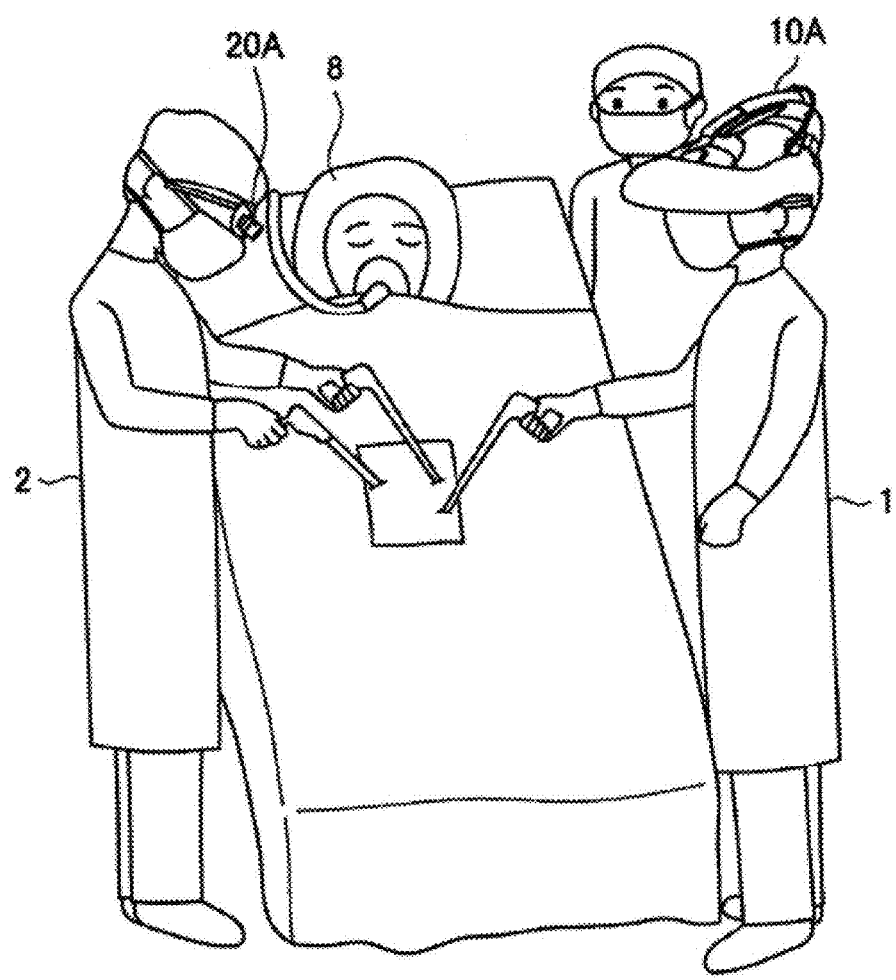
FIG. 14 is a diagram illustrating an exemplary modification example of the information processing system according to the embodiment.

Referring to FIG. 14, the information processing system 1000 will be described in which the operator 2 as the first user wears the loupe-type first display unit 20A and the assistant 1 as the second user wears an HMD-type second display unit 10A. FIG. 14 is a diagram illustrating an outline of the information processing system 1000 in a case where the operator 2 wears the loupe-type first display unit 20A and the assistant 1 wears the HMD-type second display unit 10A.

In FIG. 14, the assistant 1 and the operator 2 surround the patient 8 to perform the surgery. The surgery may be, for example, the brain surgery. The operator 2 wears the loupe-type first display unit 20A. The assistant 1 performs the surgery while looking through the HMD-type second display unit 10A. The loupe-type first display unit 20A is provided with the loupe built-in camera (not illustrated) as the local coordinate camera. The HMD-type second display unit 10A worn by the assistant 1 may be a transmission type or video-see-through type display unit. In the information processing system 1000, the position detection device 330 that detects a position and an attitude of the HMD-type second display unit 10A is further installed in the external environment such as the operating room, making it possible to detect the position and the attitude of the HMD-type second display unit 10A.

The loupe-type first display unit 20A is further provided with the loupe built-in eye gaze detector (not illustrated) as the eye gaze detection device 310. The position detection device 330 that performs the imaging of the loupe-type first display unit 20A may be installed in the external environment such as the operating room.

The captured image captured by the loupe built-in camera may be displayed on the loupe-type first display unit 20A. Further, in a display region of the HMD-type second display unit 10A, the captured image is displayed as the affected site region as viewed from the HMD-type second display unit 10A worn by the assistant 1, in view of a relationship between a position and an attitude of the loupe built-in camera and the position and the attitude of the HMD-type second display unit 10A.

On the basis of pieces of information acquired from the eye gaze detection device 310, the local coordinate camera 320, and the position detection device 330, the HMD-type second display unit 10A displays the captured image, thereby visualizing and displaying the movement history of the gazing point of the operator 2.

(4.3. Operator Wears HMD-Type Display Unit)

Figure 15:
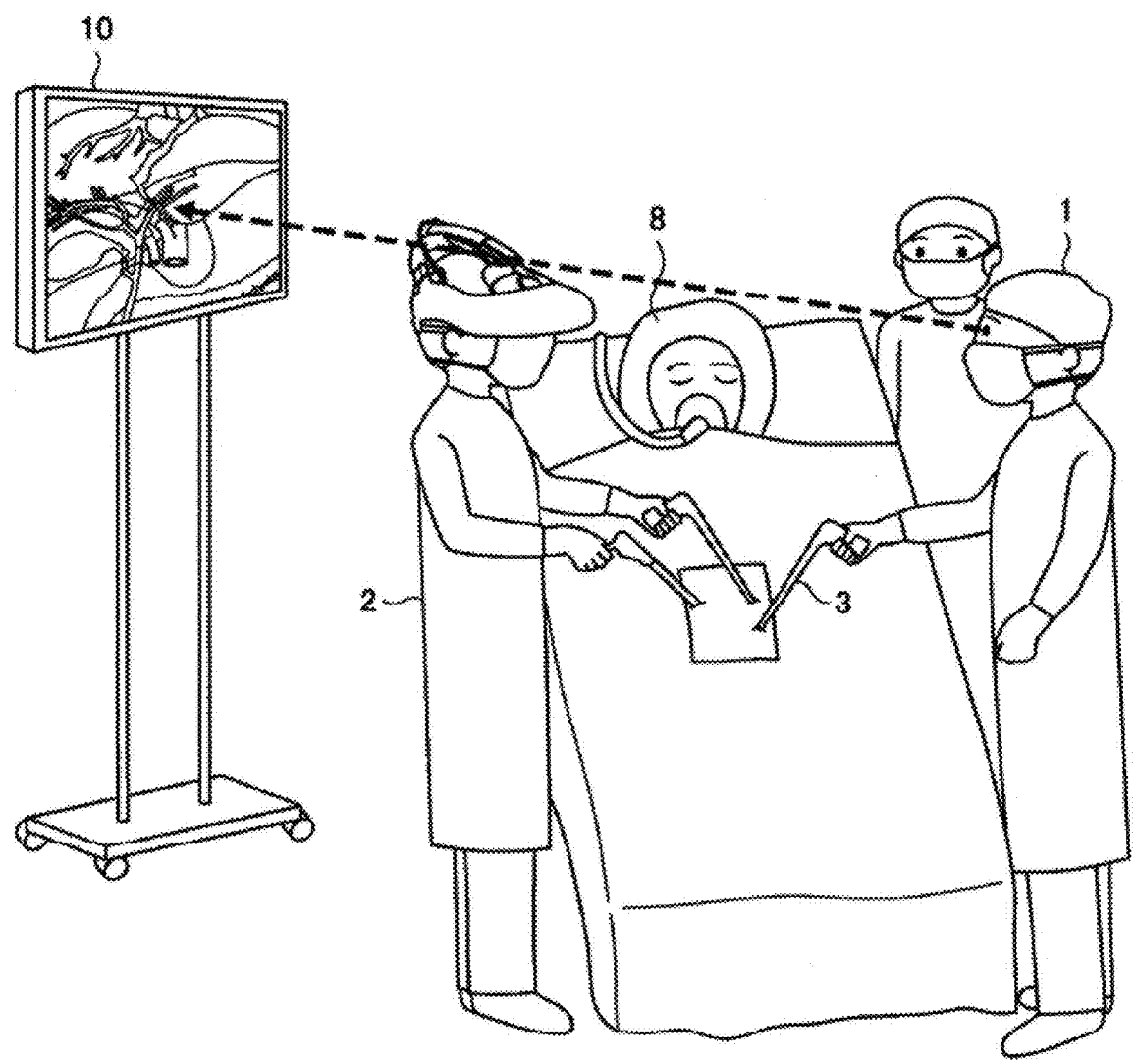
FIG. 15 is a diagram illustrating an exemplary modification example of the information processing system according to the embodiment.

Referring to FIG. 15, the information processing system 1000 will be described in which the operator 2 as the first user wears the HMD-type first display unit and the assistant 1 as the second user visually recognizes the assistant monitor 10. FIG. 15 is a diagram illustrating an outline of the information processing system 1000 in a case where the operator 2 wears the HMD-type first display unit 20A and the assistant 1 visually recognizes the assistant monitor 10.

In FIG. 15, the assistant 1 and the operator 2 surround the patient 8 to perform the endoscopic surgery. The assistant 1 controls the endoscope 3, and the captured image captured by the endoscope 3 is displayed on the assistant monitor 10. At this time, the captured image is displayed in the display region of the HMD-type first display unit 20A worn by the operator 2. The gazing point of the operator 2 is grasped by detecting the eye gaze information of the operator 2 by the eye gaze detection device 310 incorporated in the HMD-type first display unit 20A worn by the operator 2. The assistant monitor 10 displays the captured image and the movement history of the gazing point of the operator 2. Note that, instead of visually recognizing the assistant monitor 10, the assistant 1 may visually recognize the captured image by wearing the HMD-type display unit as with the operator 2.

(4.4. Operator and Assistant Operate Microscope)

Figure 16:
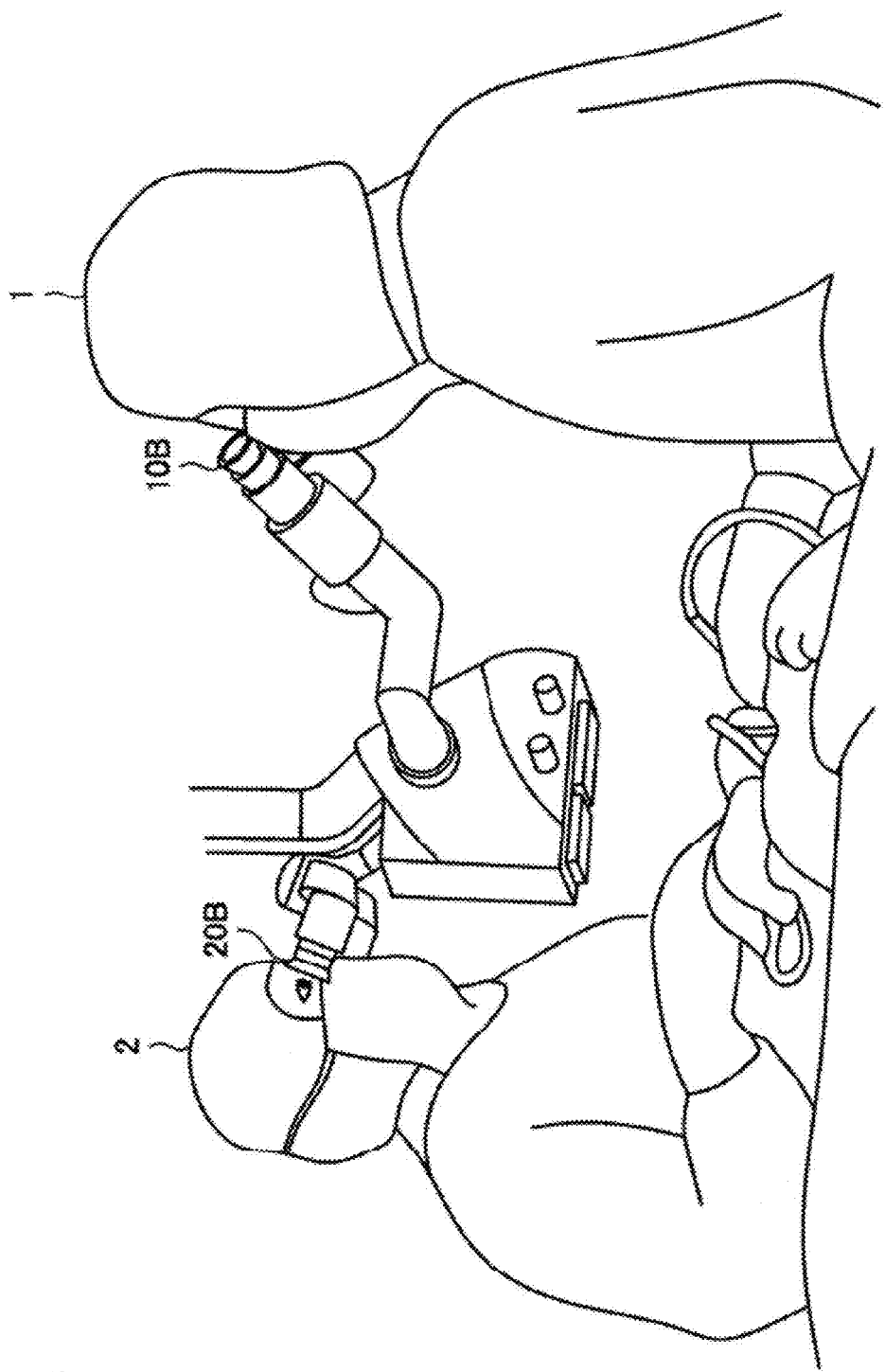
FIG. 16 is a diagram illustrating an exemplary modification example of the information processing system according to the embodiment.

Referring to FIG. 16, a case will be described in which the operator 2 as the first user and the assistant 1 as the second user perform the surgery on the patient via a medical microscope. For example, in the brain surgery or the like, the surgery may sometimes be performed using a microscope.

In a case of the microscope, instead of the endoscope 3 described above, the imaging unit is a microscope built-in camera that is built into the microscope. The position detection device that detects a position and an attitude of the microscope-built-in camera may be built in the microscope as well, or may be installed in the external environment for detection thereof.

The operator 2 visually recognizes the captured image through a display region of a microscope eyepiece 20B provided on the microscopic. In addition to the microscopic eyepiece 20B, the microscope is provided with a microscope built-in eye gaze detector as the eye gaze detection device, which enables the eye gaze detection of the operator 2.

The movement history of the gazing point of the operator 2 is visualized and displayed in the display region of the microscopic eyepiece 10B provided on the microscope. In the present embodiment, the movement history is visualized in the display region of the microscopic eyepiece 10B for the assistant, but the movement history may be displayed in a display region such as a monitor that is not provided in the microscope.

(5. Hardware Configuration Example)

Figure 17:
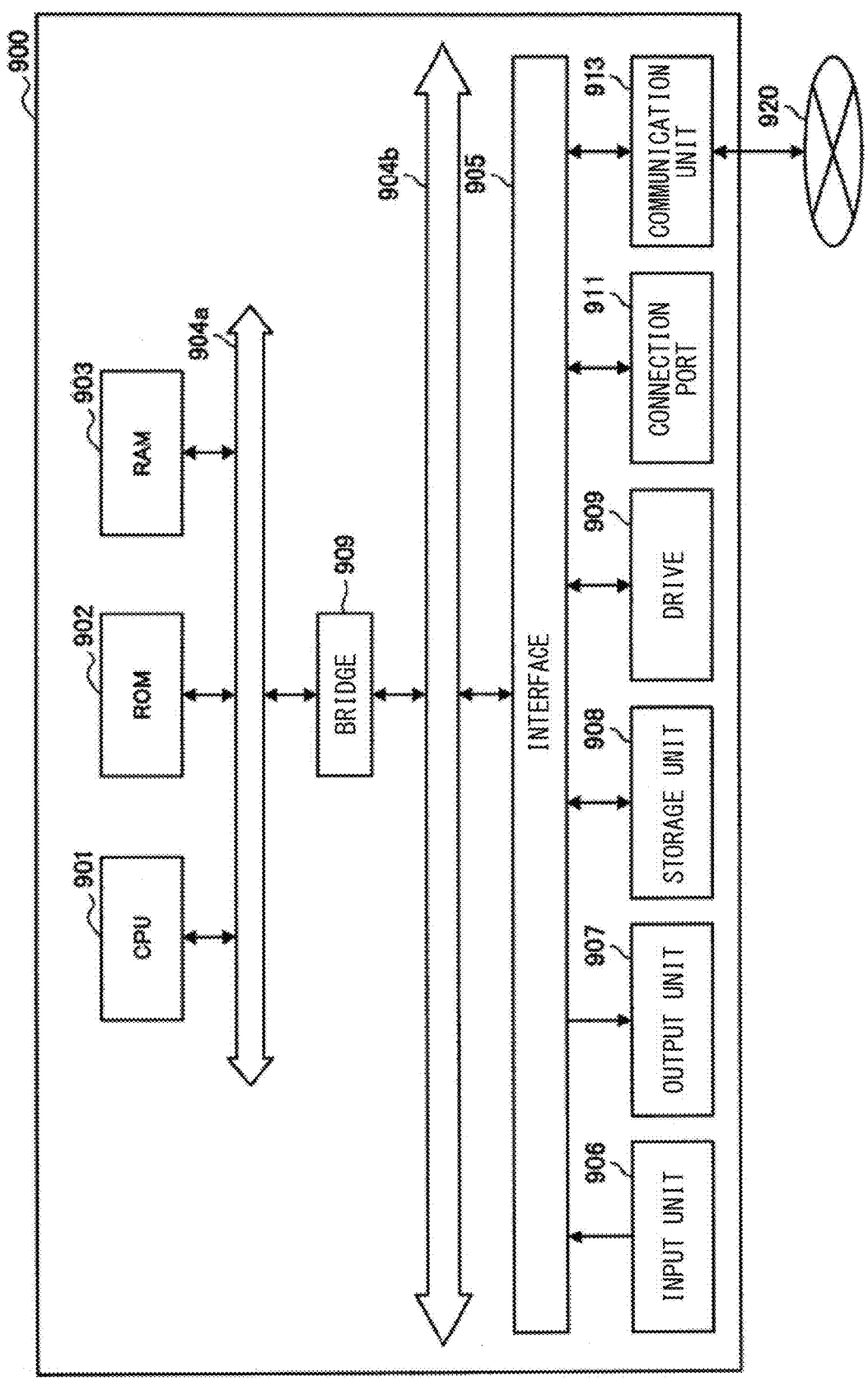
FIG. 17 is a diagram illustrating an exemplary configuration of hardware of the information processing system according to the embodiment.

Referring to FIG. 17, an exemplary hardware configuration of the information processing apparatus included in the information processing system according to the present embodiment will be described. FIG. 17 is a block diagram illustrating an example of the hardware configuration of the information processing apparatus according to the present embodiment. Note that an information processing apparatus 900 illustrated in FIG. 17 may be included in the information processing system 1000 illustrated in FIG. 2, for example. An information process to be performed by the information processing system 1000 according to the present embodiment is achieved in cooperation with software and hardware described below.

As illustrated in FIG. 17, the information processing apparatus 900 includes a CPU (Central Processing Unit) 901, a ROM (Read Only Memory) 902, a RAM (Random Access Memory) 903, and a host bus 904a. Further, the information processing apparatus 900 includes a bridge 904, an external bus 904b, an interface 905, an input unit 906, a display unit 907, a storage unit 908, a drive 909, a connection port 911, and a communication unit 913. The information processing apparatus 900 may include a processing circuit such an electric circuit, a DSP, or an ASIC in place of or in conjunction with the CPU 901.

The CPU 901 functions as an arithmetic processing unit and a control unit, and controls overall operations in the information processing apparatus 900 in accordance with various programs. Further, the CPU 901 may be a microprocessor. The ROM 902 stores programs, arithmetic parameters, etc. that the CPU 901 uses. The RAM 903 temporarily stores a program that is used in execution of the CPU 901, parameters that change appropriately in execution thereof, and the like. The CPU 901 may form, for example, the movement history calculator 210 or the display controller 120 illustrated in FIG. 2.

The CPU 901, the ROM 902, and the RAM 903 are connected to each other by the host bus 904a including a CPU bus and the like. The host bus 904a is connected to the external bus 904b such as a PCI (Peripheral Component Interconnect/Interface) bus via the bridge 904. Note that the host bus 904a, the bridge 904, and the external bus 904b are not necessarily configured separately, and these functions may be packaged in a single bus.

The input unit 906 is implemented by, for example, a unit through which the user inputs information, such as a mouse, a keyboard, a touch panel, a button, a microphone, a switch, or a lever. Further, the input unit 906 may be a remotecontrol unit that uses infrared ray or other electromagnetic waves, or may be external connection equipment such as a mobile phone or a PDA compatible with operations of the information processing apparatus 900. Further, the input unit 906 may include, for example, an input control circuit or the like that generates an input signal on the basis of information inputted by the user using the input means described above and outputs the generated input signal to the CPU 901. It is possible for the user of the information processing apparatus 900 to input various data or provide instructions for a processing operation to the information processing apparatus 900 by operating the input unit 906.

The display unit 907 is formed by a unit that is able to notify the user of acquired information visually or audibly. Examples of such a unit include displays such as a CRT display, a liquid crystal display, a plasma display, an EL display, a laser projector, an LED projector, or a lamp, and sound output units such as a speaker or a headphone. The display unit 907 outputs, for example, results obtained through various processes performed by the information processing apparatus 900. Specifically, the display unit 907 visually displays the results obtained through various processes performed by the information processing apparatus 900 in a variety of formats, such as text, images, tables, graphs, etc. Meanwhile, the sound output unit converts audio signals including reproduced sound data, acoustic data or the like into analog signals and outputs the analog signals audibly. The display unit 907 visualizes and displays the movement history of the gazing point acquired by the movement history acquiring section 110 illustrated in FIG. 2.

The storage unit 908 is a data storing unit formed as an example of a memory section of the information processing apparatus 900. The storage unit 908 is implemented by, for example, a magnetic memory section device such as an HDD, a semiconductor memory device, an optical memory device, a magneto-optical memory device, or the like. The storage unit 908 may include a storage medium, a recording unit for recording data on the storage medium, a reading unit for reading data from the storage medium, a deletion unit for deleting data recorded on the storage medium, etc. The storage unit 908 stores a program to be executed by the CPU 901, various data, and various externally acquired data, etc. The storage unit 908 stores, for example, various parameters and the like used when the movement history of the gazing point is to be calculated by the movement history calculator 210 illustrated in FIG. 2.

The drive 909 is a reader/writer for a storage medium, and is incorporated in or externally attached to the information processing apparatus 900. The drive 909 reads information recorded on a removable storage medium mounted thereon, such as a magnetic disk, an optical disk, a magneto-optical disk, or a semiconductor memory, and outputs the information to the RAM 903. The drive 909 is also able to write information on the removable storage medium.

The connection port 911 is an interface to be connected to external equipment, and is a connector to the external equipment that is able to transmit data through, for example, a USB (Universal Serial Bus) or the like.

The communication unit 913 is, for example, a communication interface formed by a communication unit or the like for connection to a network 920. The communication unit 913 may be, for example, a communication card or the like for wired or wireless LAN (Local Area Network), LTE (Long Term Evolution), Bluetooth (registered trademark), or WUSB (Wireless USB). Further, the communication unit 913 may be a router for optical communication, a router for ADSL (Asymmetric Digital Subscriber Line), modems for various types of communications, or the like. The communication unit 913 is able to transmit and receive signals or the like to and from the Internet or other communication equipment in accordance with predetermined protocols such as TCP/IP, for example. The communication unit 913 is provided in, for example, various configurations illustrated in FIG. 2, and allows for communication between the eye gaze detection device 310, the local coordinate camera 320, and the position detection device 330 and the movement history calculator 210. In addition, the communication unit 913 also enables communication between the movement history calculator 210 and the information processing apparatus 100. Furthermore, the communication unit 913 enables communication between the information processing apparatus 100 and the display unit 10 as well.

Note that the network 920 is a wired or wireless transmission path for information transmitted from units connected to the network 920. For example, the network 920 may include a public network such as the Internet, a telephone network or a satellite communication network, various LANs (Local Area Networks) including Ethernet (registered trademark), WAN (Wide Area Network), and the like. Further, the network 920 may include a dedicated line network such as an IP-VPN (Internet Protocol-Virtual Private Network).

Further, in the information processing apparatus 900, it is possible to create a computer program for causing the hardware such as a CPU, a ROM, or a RAM incorporated in the information processing system 1000 to perform functions equivalent to the configurations of the information processing system 1000 according to the present embodiment described above. A recording medium storing the computer program may also be included in the scope of a technique according to the present disclosure.

As above, the preferred embodiment of the present disclosure has been described in detail with reference to the accompanying drawings; however, the technical scope of the present disclosure is not limited to these examples. It is apparent that those having ordinary skill in the technical field of the present disclosure could easily arrive at various modified examples or revised examples within the meaning of the technical concept recited in claims, and it is understood that these also should naturally fall under the technical scope of the present disclosure.

For example, in the above embodiment, the operator and the assistant in the scene of the surgery in the medical field are taken as an example, but the present technology is not limited to such an example. For example, the present technology may be used in any use in presenting the movement history of the gazing point of the first user to the second user. Specifically, the present technology may be used in the field of education. In a case where a student performs learning such as surgery, it is possible for the student to intuitively understand a point to be gazed at the time of the surgery by learning through a picture on which the movement history of the gazing point of the operator is displayed, thereby enabling effective learning. Meanwhile, it is possible for an instructor to instruct, for example, a timing and where to gaze by understanding the movement history of the gazing point of the student.

For example, the present technology may also be used to prevent overlooking or the like upon monitoring of a surveillance camera in a monitoring room. In a case of monitoring of the surveillance camera, in the display region of the captured image captured by the surveillance camera, the gazing region of an observer indicates that the surveillance has been performed, and the region other than the gazing region indicates that the surveillance has not yet been performed. Thus, it is possible to perform the monitoring more finely by prompting the monitoring of the region other than the gazing region. Therefore, by applying a technique of the present disclosure, it is possible to achieve an effect of preventing overlooking of the surveillance camera through attracting the attention of the observer to the region other than the gazing region, by changing the display style so that the visibility of the region other than the gazing region becomes high and the visibility of the gazing region becomes low. In particular, in a case where there are multiple observers, it is possible to prevent overlapping of the gazing points by displaying the movement history of the gazing point gazed by each of the observers, thereby making it possible to efficiently perform the surveillance operation. As a type of the display style, the movement history of the gazing point may be displayed in monochrome and the display region other than the gazing region may be displayed in color to enhance visibility in a case of the surveillance camera.

Furthermore, the effects described in the present specification are only explanatory or exemplary and not limitative. That is, a technique according to the present disclosure may achieve other effects that should be apparent from the description of the present specification by those skilled in the art in addition to the above-described effects or instead of the above-described effects.

It is to be noted that the following configurations also fall within the technical scope of the present disclosure.

(1)
An information processing apparatus including:
a movement history acquiring section that acquires a movement history, based on an absolute coordinate, of a gazing point of a first user that gazes at a display region, the absolute coordinate being in a three-dimensional space displayed in the display region; and
a display controller that controls a display unit that displays the display region to visualize, to a second user, the movement history of the gazing point.

(2)
The information processing apparatus according to (1), in which the movement history is calculated on a basis of: eye gaze information of the first user to the display unit that displays the display region; and a position and an attitude of an imaging unit that captures an image of the display region.

(3)
The information processing apparatus according to (1) or (2), in which the display region to be gazed by the first user is displayed on a display unit that is different from the display unit to be controlled by the display controller.

(4)
The information processing apparatus according to (2), in which the movement history is derived by converting a local coordinate into the absolute coordinate, the local coordinate being based on the imaging unit and estimated using: the eye gaze information of the first user; and depth information of the display region.

(5)
The information processing apparatus according to any one of (1) to (4), in which the movement history includes predetermined number of the gazing points.

(6)
The information processing apparatus according to any one of (1) to (5), in which the display controller displays, in different display styles, a gazing region that includes the gazing point in the display region and a region other than the gazing region.

(7)
The information processing apparatus according to (6), in which visibility of the gazing region is higher than visibility of the region other than the gazing region.

(8)
The information processing apparatus according to (7), in which the gazing region is to be displayed in color and the region other than the gazing region is to be displayed in monochrome.

(9)
The information processing apparatus according to (7), in which brightness of the gazing region is higher than brightness of the region other than the gazing region.

(10)
The information processing apparatus according to (7), in which resolution of the gazing region is higher than resolution of the region other than the gazing region.

(11)
The information processing apparatus according to (2), in which the display region includes an affected site region of a patient, the first user includes an operator, the second user includes an assistant that operates the imaging unit that captures the image of the display region, and the imaging unit includes a medical imaging unit.

(12)
The information processing apparatus according to (11), in which the imaging unit includes an endoscope.

(13)
The information processing apparatus according to (3), in which a first display unit to be controlled by the display controller includes a wearable display unit to be worn by the first user.

(14)
The information processing apparatus according to (3), in which a second display unit that is different from a first display unit to be controlled by the display controller includes a wearable display unit to be worn by the second user.

(15)
The information processing apparatus according to (3), in which a first display unit to be controlled by the display controller and a second display unit that is different from the first display unit are provided in a medical microscope.

(16)
An information processing method that causes a processor to execute a process, the process including:
acquiring a movement history, based on an absolute coordinate, of a gazing point of a first user that gazes at a display region, in which the absolute coordinate is in a three-dimensional space displayed in the display region; and
controlling a display unit that displays the display region to visualize, to a second user, the movement history of the gazing point.

(17)
A program that causes a computer to function as:
a movement history acquiring section that acquires a movement history, based on an absolute coordinate, of a gazing point of a first user that gazes at a display region, in which the absolute coordinate is in a three-dimensional space displayed in the display region; and a display controller that controls a display unit that displays the display region to visualize, to a second user, the movement history of the gazing point.

DESCRIPTION OF SYMBOLS

2 Operator
3 Endoscope
4 Organ
8 Patient
10 Assistant monitor (Display unit)
10A Second display unit
10B Microscope eyepiece
20 Operator monitor
20A First display unit
20B Microscope eyepiece
21 Display region
100 Information processing apparatus
110 Movement history acquiring section
111 Viewing range
112 Gazing direction
113 Gazing point
120 Display controller
122, 122a, 122b, 122c Gazing region
210 Movement history calculator
310 Eye gaze detection device
320 Local coordinate camera
330 Position detection device

The invention claimed is:

1. An information processing apparatus, comprising:
circuitry configured to:
acquire eye gaze information indicating a gazing direction of a first user toward a first display unit that displays a display region;
acquire information indicating a position and an attitude of an imaging unit that captures an image of the display region;
calculate a movement history of a gazing point of the first user that gazes at the display region, wherein
the movement history of the gazing point is calculated based on the eye gaze information and the information indicating the position and the attitude of the imaging unit, and
the gazing point has an absolute coordinate in a three-dimensional space displayed in the display region; and
control the first display unit to display the display region to visualize, to a second user, the movement history of the gazing point.

2. The information processing apparatus according to claim 1, wherein the display region gazed by the first user is displayed on a second display unit that is different from the first display unit.

3. The information processing apparatus according to claim 2, wherein the first display unit comprises a wearable display unit wearable by the first user.

4. The information processing apparatus according to claim 2, wherein the second display unit that is different from the first display unit comprises a wearable display unit wearable by the second user.

5. The information processing apparatus according to claim 2, wherein the first display unit and the second display unit that is different from the first display unit are provided in a medical microscope.

6. The information processing apparatus according to claim 1, wherein the circuitry is further configured to:

estimate a local coordinate of the gazing point based on the eye gaze information of the first user and depth information of the display region; and
convert the local coordinate of the gazing point into the absolute coordinate.

7. The information processing apparatus according to claim 6, wherein the movement history includes a specific number of gazing points.

8. The information processing apparatus according to claim 7, wherein the circuitry is further configured to control the first display unit to display, in different display styles, a gazing region that includes the gazing point in the display region and a region different from the gazing region.

9. The information processing apparatus according to claim 8, wherein a visibility of the gazing region is higher than a visibility of the region different from the gazing region.

10. The information processing apparatus according to claim 9, wherein the circuitry is further configured to control the first display unit to display the gazing region in color and the region different from the gazing region in monochrome.

11. The information processing apparatus according to claim 9, wherein a brightness of the gazing region is higher than a brightness of the region different from the gazing region.

12. The information processing apparatus according to claim 9, wherein a resolution of the gazing region is higher than a resolution of the region different from the gazing region.

13. The information processing apparatus according to claim 1, wherein
the display region comprises an affected site region of a patient,
the first user comprises an operator,
the second user comprises an assistant that operates the imaging unit that captures the image of the display region, and
the imaging unit comprises a medical imaging unit.

14. The information processing apparatus according to claim 13, wherein the medical imaging unit comprises an endoscope.

15. An information processing method comprising:
acquiring eye gaze information indicating a gazing direction of a first user toward a display unit that displays a display region;
acquiring information indicating a position and an attitude of an imaging unit that captures an image of the display region;
calculating a movement history of a gazing point of the first user that gazes at the display region, wherein
the movement history of the gazing point is calculated based on the eye gaze information and the information indicating the position and the attitude of the imaging unit, and
the gazing point has an absolute coordinate in a three-dimensional space displayed in the display region; and
controlling the display unit to display the display region to visualize, to a second user, the movement history of the gazing point.

16. A non-transitory computer-readable medium having stored thereon computer-executable instructions which, when executed by a computer, cause the computer to execute operations, the operations comprising:
acquiring eye gaze information indicating a gazing direction of a first user toward a display unit that displays a display region;

acquiring information indicating a position and an attitude of an imaging unit that captures an image of the display region;

calculating a movement history of a gazing point of the first user that gazes at the display region, wherein the movement history of the gazing point is calculated based on the eye gaze information and the information indicating the position and the attitude of the imaging unit, and the gazing point has an absolute coordinate in a three-dimensional space displayed in the display region; and controlling the display unit to display the display region to visualize, to a second user, the movement history of the gazing point.

* * * * *